US006765217B1

(12) United States Patent
Nishimura et al.

(10) Patent No.: US 6,765,217 B1
(45) Date of Patent: Jul. 20, 2004

(54) CHARGED-PARTICLE-BEAM MAPPING PROJECTION-OPTICAL SYSTEMS AND METHODS FOR ADJUSTING SAME

(75) Inventors: Hiroshi Nishimura, Zushi (JP); Naoto Kihara, Yokohama (JP); Kinya Kato, Yokohama (JP); Toru Takagi, Kawasaki (JP); Akihiro Goto, Tokyo (JP); Junji Ikeda, Yokohama (JP); Kazuya Okamoto, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/302,075

(22) Filed: Apr. 28, 1999

(51) Int. Cl.$^7$ ............................................... G01N 21/00
(52) U.S. Cl. .................................. 250/491.1; 250/492.2
(58) Field of Search ........................... 250/491.1, 492.2

(56) References Cited

U.S. PATENT DOCUMENTS 6,107,636 A * 8/2000 Muraki ..................... 250/492.2

OTHER PUBLICATIONS

Tsuno, "Simulation of a Wien Filter as Beam Separator in a Low Energy Electron Microscope," *Ultramicroscopy* 55:127–140 (1994).

* cited by examiner

Primary Examiner—John R. Lee
Assistant Examiner—James Leybourne
(74) Attorney, Agent, or Firm—Klarquist Sparkman, LLP

(57) ABSTRACT

Charged-particle-beam (CPB) mapping projection-optical systems and adjustment methods for such systems are disclosed that can be performed quickly and accurately. In a typical system, an irradiation beam is emitted from a source, passes through an irradiation optical system, and enters a Wien filter ("E×B"). Upon passing through the E×B, the irradiation beam passes through an objective optical system and is incident on an object surface. Such impingement generates an observation beam that returns through the objective optical system and the E×B in a different direction to a detector via an imaging optical system. An adjustment-beam source emits an adjustment beam used for adjusting and aligning the position of, e.g., the object surface and/or the Wien's condition of the E×B. The adjustment beam can be off-axis relative to the objective-optical system. For such adjusting and aligning, fiducial marks (situated, e.g., in the plane of the object surface) can be used that are optimized for the CPB optical system and the off-axis optical system. Desirably, the image formed on the detector when electrical voltage and current are not applied to the E×B is in the same position as the image formed on the detector when electrical voltage and current are applied to the E×B. Also provided are "evaluation charts" for use in such alignments that do not require adjustment of the optical axis of the irradiation optical system, and from which the kinetic-energy distribution of the emitted adjustment beam is stable.

31 Claims, 11 Drawing Sheets

CHARGED-PARTICLE-BEAM MAPPING PROJECTION-OPTICAL SYSTEMS AND METHODS FOR ADJUSTING SAME

FIELD OF THE INVENTION

This invention pertains to, inter alia, charged-particle-beam (CPB) projection-optical systems for use in "mapping" CPB (e.g., electron beam or ion beam) microscopes, to methods for adjusting such projection-optical systems, and to use of such microscopes for observing and inspecting surfaces of objects.

BACKGROUND OF THE INVENTION

Charged-particle-beam ("CPB", e.g., electron beam or ion beam) microscopes are in routine use for observing and inspecting intricate and highly integrated semiconductor circuits and the like as formed on suitable substrates. Such CPB microscopes include scanning electron microscopes (SEMs) and "mapping electron microscopes". Whereas an SEM performs illumination and imaging from one point to another point on a specimen, a mapping electron microscope performs illumination and imaging from one surface to another surface of the specimen. Much research and development has been directed in recent years to improving the CPB mapping projection-optical systems used in mapping electron microscopes.

The structure of a conventional mapping electron microscope is summarized below, with reference to FIG. 1. A primary electron beam (also termed an "irradiation electron beam") PB is emitted by an electron gun 21. The primary electron beam PB passes through an irradiation lens system 22 and enters a Wien filter 25. The Wien filter 25 typically comprises a magnetic pole 26 and an electrical pole 27. The Wien filter 25 bends the trajectory of the primary electron beam PB. After passing through the Wien filter 25, the primary electron beam PB passes through an aligner 30 and through an objective lens system 24 so as to be incident on the surface of a specimen 23. The irradiation lens system 22, Wien filter 25, aligner 30, and objective lens system 24 are collectively termed the "irradiation optical system" or "primary optical system."

Impingement of the primary electron beam PB on the surface of the specimen 23 generates relatively high-energy electrons that are reflected from the surface of the specimen 23 and relatively low-energy secondary electrons that are emitted from the surface of the specimen 23. The secondary electrons are normally used for imaging. The secondary electrons (formed into an "observation electron beam" or "secondary electron beam" OB) returns through the objective lens system 24 and the aligner 30 and re-entered the Wien filter 25. Rather than experiencing trajectory bending by the Wien filter 25, the observation electron beam OB passes straight through the Wien filter 25. The observation electron beam OB then passes through an imaging lens system 28 and enters a detector 29. Observations of the specimen 23 are based on information in the observation electron beam OB as detected by the detectors 29. The objective lens system 24, aligner 30, Wien filter 25, and imaging lens system 28 collectively comprise a "mapping optical system" or "secondary optical system."

The Wien filter 25 is an electromagnetic prism also termed "E×B" ("E cross B"). By imposing Wien's condition on the primary electron beam PB, the Wien filter 25 imparts a desired deflection to the trajectory of the primary electron beam PB, while not deflecting the trajectory of the secondary electron beam OB. Upon passing through the Wien filter 25, the primary electron beam PB can have, e.g., a linear, rectangular, circular, or elliptical transverse (sectional) profile.

It is necessary to be able to accurately adjust various components of the CPB mapping projection-optical system (e.g., align the illumination field of the primary optical system with the observation field of the secondary optical system) before use in order to accurately observe and inspect the surface of the specimen 23. To such end, it would be advantageous to be able to independently adjust (e.g., alignment with optical axis, aberration correction) the primary optical system, the secondary optical system, and the Wien filter 25 (e.g., by adjusting respective voltages (or currents) applied to components in the primary optical system, the secondary optical system, and the cathode lens, and by adjusting the electromagnetic field generated by the Wien filter 25). Conventional adjustment methods require excessive time and effort to perform.

It also would be advantageous to be able to determine positional coordinates of the specimen being observed or inspected using a CPB mapping microscope. According to one conventional scheme for making such a determination, an off-axis light-optical system (i.e., an optical system for light) is used in conjunction with the CPB optical system. In such a scheme, the specimen is mounted on a stage provided with fiducial marks (e.g., a pattern of lines and spaces). Unfortunately, however, conventional practice has revealed much difficulty in detecting such marks using both a light-optical system and a CPB optical system. Difficulty is also conventionally encountered in detecting fiducial marks configured as a grooved pattern (e.g., scribe lines), which readily can be detected using an optical microscope but not by a CPB optical system.

In other words, marks that can be detected readily using light are usually not detectable using a charged particle beam. This makes it difficult to select a fiducial mark that is optimal for use with both a CPB optical system and an off-axis light-optical system.

According to another conventional method for evaluating optical performance (e.g., resolution and aberration) of a CPB mapping microscope an "evaluation chart" is placed at the position of the specimen 23 in FIG. 1. The evaluation chart is typically a pattern comprising ultra-fine features defined by deposition or microlithography. The evaluation chart is irradiated using the primary electron beam PB, and an image is produced from the observation beam OB generated therefrom.

Unfortunately, whenever optical performance is evaluated using an evaluation chart in such a manner, the optical axis of the irradiation optical system and the optical axis of the mapping optical system must be simultaneously adjusted by making simultaneous adjustments to the Wien filter and the aligner. This requires that the evaluation chart be uniformly illuminated with the primary electron beam PB in order to check the optical performance of the mapping electron microscope. The Wien's condition is found while continuously changing the electromagnetic pole induction parameters in the Wien filter 25 so that the trajectory of the secondary electron beam is not deflected. Changing the electromagnetic pole induction parameters in such a manner causes a simultaneous change in the uniformity of illumination by the primary electron beam. Consequently, it is necessary to continually readjust the optical axis of the illumination optical system. In addition, whenever the secondary electron beam is deflected by the aligner and axially aligned with the objective lens system, the primary electron beam is simultaneously deflected, thereby changing the uniform illumination and making it necessary again to readjust the optical axis of the illumination optical system. Thus, such conventional evaluations of optical performance are extremely complex to perform.

The kinetic-energy distribution of electrons in the secondary electron beam emitted from the specimen is very sensitively affected by the type and shape of the specimen and the irradiation angle of the secondary electron beam. This instability of the kinetic-energy distribution of the secondary electron beam adds even more complexity to conventional evaluations of the optical performance of the mapping electron microscope, and makes it impossible to determine, e.g., the magnitude of chromatic aberration.

SUMMARY OF THE INVENTION

The shortcomings of the prior art noted above are addressed by the present invention which provides, inter alia, apparatus for charged-particle-beam (CPB) projection-optical systems, and methods for adjusting such systems, allowing rapid and accurate adjustments, even by a relatively unskilled operator.

According to one aspect of the invention, charged-particle-beam mapping projection-optical systems are provided. Representative embodiments of such systems comprise an irradiation optical system, an E×B beam separator (i.e., Wien filter or "E×B"), an objective optical system, an imaging optical system, and an adjustment-beam source. The irradiation-optical system directs an irradiation charged particle beam along a first axis from an irradiation-beam source. The E×B beam separator is configured and situated to receive the irradiation beam from the irradiation optical system and to direct the irradiation beam downstream of the E×B beam separator. The objective optical system is configured and situated to receive the irradiation beam from the E×B beam separator, direct the irradiation beam to be incident on a surface of a specimen located at a position downstream of the objective optical system, receive an observation charged particle beam generated by impingement of the irradiation beam on the specimen surface, and direct the observation beam to the E×B beam separator. The E×B beam separator causes the observation beam to propagate along a second axis having a direction different than the first axis. The imaging optical system is configured and situated to receive the observation beam from the E×B beam separator and to direct the observation beam from the E×B beam separator to a detector. The adjustment-beam source is configured to emit an adjustment charged particle beam, and is situatable at the specimen position so as to direct the adjustment beam, in place of the observation beam, through the objective and imaging optical systems to the detector.

The adjustment beam produced by the adjustment-beam source has an emission profile at the specimen position. The emission profile desirably corresponds to at least one of a dot, a line, a plane, a cross, or an L-shaped profile.

The adjustment beam can be any of various charged particle beams, such as an electron beam. The adjustment-beam source desirably produces the adjustment beam having a kinetic energy equal to a kinetic energy of the observation beam as generated at the specimen surface. An exemplary adjustment-beam source is a cold cathode. To provide an acceleration of the adjustment beam as it propagates to the detector, an electrode can be situated object-wise of the objective optical system so as to generate a potential relative to the adjustment-beam source sufficient to accelerate the adjustment beam as the adjustment beam propagates to the detector.

According to another aspect of the invention, methods are provided for operating a charged-particle-beam mapping projection microscope. In representative embodiments of such methods, an irradiation charged particle beam is directed along a first axis from an irradiation-beam source through an irradiation optical system to an E×B beam separator, then passed through the E×B beam separator and through an objective optical system so as to cause the irradiation beam to impinge on a surface of a specimen at an object surface. Such impingement generates, from the impingement, an observation charged particle beam propagating from the specimen toward the objective optical system. The observation beam is passed through the objective optical system and the E×B beam separator along a second axis having a different direction than the first axis, and then through an imaging optical system to a detector. The subject methods comprise a process for adjusting the objective optical system and imaging optical system. In such an adjustment process, the specimen (situated at the object surface) is replaced with an adjustment-beam source that emits an adjustment charged particle beam. While passing the adjustment beam through the objective optical system, the E×B beam separator, and the imaging optical system, electrical power is applied only to the objective optical system. Meanwhile, one or more of an axial alignment and an aberration characteristic of the objective optical system is determined. If desired or required, the one or more of an axial alignment and an aberration characteristic of the objective optical system can be adjusted based on the determination.

Electrical power can be applied to the imaging optical system as well as the objective optical system, during which one or more of an axial alignment and an aberration characteristic of the imaging optical system is determined. If desired or required, the one or more of an axial alignment and an aberration characteristic of the imaging optical system can be adjusted based on the determination.

According to another aspect of the invention, CPB mapping projection-optical systems are provided. Representative embodiments of such systems comprise an irradiation optical system, an E×B beam separator, an objective optical system, an imaging optical system, an alignment-beam source, and an alignment optical system. The irradiation optical system directs an irradiation charged particle beam along a first axis from an irradiation-beam source. The E×B beam separator is configured and situated so as to receive the irradiation beam from the irradiation optical system and to direct the irradiation beam downstream of the E×B beam separator. The objective optical system is configured and situated to receive the irradiation beam from the E×B beam separator, direct the irradiation beam to be incident on a specimen surface located at an object-surface plane downstream of the objective optical system, receive an observation charged particle beam generated by impingement of the irradiation beam on the specimen surface, and direct the observation beam to the E×B beam separator, wherein the E×B beam separator causes the observation beam to propagate along a second axis having a direction different than the first axis. The imaging optical system is configured and situated and receive the observation beam from the E×B beam separator and to direct the observation beam from the E×B beam separator to a first detector. The alignment-beam source is configured to emit an alignment beam with respect to the object-surface so as to cause the alignment beam to acquire data regarding an alignment characteristic of the object surface. The alignment optical system is situated off-axis from the objective and imaging optical systems and is configured to direct the alignment beam from the object surface to a second detector that detects the data.

The alignment-beam source can be situated at and movable within the object-surface plane. For example, the alignment-beam source can be defined on a fiducial plate, and the fiducial plate can comprise a fiducial mark. In another embodiment, the alignment-beam source is situated remotely from the object-surface plane and is directed by a lens to the object surface. In the latter instance, a fiducial mark can be situated on the object-surface plane. The fiducial mark is desirably configured to be optimal for the irradiation optical system, the objective optical system, the imaging optical system, and the off-axis optical system.

By way of example, the alignment beam can be a beam of light or a charged particle beam. In the latter instance, the alignment beam can be an electron beam, wherein the off-axis optical system is a scanning electron microscope, and the alignment-beam source desirably has an emission profile (at the object surface) that is at least one of a dot, a line, a cross, or an L-shaped profile. As a charged particle beam, the alignment beam desirably has a kinetic energy equal to the kinetic energy of the observation beam. To produce a CPB alignment beam, the alignment-beam source can be a cold cathode.

In addition, an electrical potential can be imposed between the alignment-beam source and an object-wise surface of the objective optical system. In such an instance, the potential causes an acceleration of the alignment beam as the alignment beam propagates through the objective optical system.

According to another aspect of the invention, methods are provided for operating a charged-particle-beam mapping projection microscope. In such methods, an irradiation charged particle beam is directed along a first axis from an irradiation-beam source through an irradiation optical system to an E×B beam separator, then passed through the E×B beam separator and through an objective optical system so as to cause the irradiation beam to impinge on a surface of a specimen at an object surface. Such impingement generates an observation charged particle beam propagating from the specimen toward the objective optical system. The observation beam is passed through the objective optical system and the E×B beam separator along a second axis having a different direction than the first axis, and then through an imaging optical system to a detector. In such methods, a process is provided for adjusting the objective optical system and the imaging optical system. A representative embodiment of such a process comprises placing an adjustment-beam source at the object surface (the adjustment-beam source being operable to emit an adjustment charged particle beam). An electrical potential and electrical current applied to the E×B beam separator are adjusted so as to align an image formed on the detector by the adjustment-beam source when an electrical potential and electrical current are not applied to the E×B beam separator with an image formed on the detector by the adjustment-beam source when an electrical potential and electrical current are applied to the E×B beam separator. The imaging optical system can comprise a stigmator that corrects aberration in the image formed on the detector. Also, electrical energy applied to at least one of the objective optical system and the imaging optical system can be adjusted while adjusting the electrical energy applied to the detector.

By way of example, the adjustment beam can be an electron beam. In such an instance, the adjustment beam desirably has a kinetic energy equal to the kinetic energy of the observation beam.

The process can further comprise providing a potential difference between the adjustment-beam source and a specimen-wise surface of the objective optical system, wherein the potential difference serves to accelerate the adjustment beam.

According to another aspect of the invention, CPB mapping projection-optical systems are provided, that comprise an irradiation optical system, an E×B beam separator, an objective optical system, an imaging optical system, and an adjustment-beam source. The irradiation optical system directs an irradiation charged particle beam along a first axis from an irradiation-beam source. The E×B beam separator is configured and situated to receive the irradiation beam from the irradiation optical system and to direct the irradiation beam downstream of the E×B beam separator. The objective optical system is configured and situated to receive the irradiation beam from the E×B beam separator, direct the irradiation beam to be incident on a specimen surface located at an objective-surface plane downstream of the objective optical system, receive an observation charged particle beam generated by impingement of the irradiation beam on the specimen surface, and direct the observation beam to the E×B beam separator, wherein the E×B beam separator causes the observation beam to propagate along a second axis having a direction different than the first axis; the imaging optical system is configured and situated to receive the observation beam from the E×B beam separator and to direct the observation beam from the E×B beam separator to a first detector. The adjustment-beam source is configured to emit an adjustment beam with respect to the object-surface so as to cause the adjustment beam to acquire data regarding a position of the object surface. Desirably, the E×B beam separator is connected to a variable-power supply to permit an electrical potential and electrical current applied to the E×B beam separator to be adjusted as required such that an image formed on the detector by the adjustment beam when the electrical potential and electrical current are not applied to the E×B beam separator is aligned with an image formed on the detector by the adjustment beam when the electrical potential and electrical current are applied to the E×B beam separator.

Preferably, the imaging optical system includes stigmators that correct aberration in the image formed on the detector. In the method, the voltage (or current) applied to at least one of the objective optical system and the imaging optical system is adjusted while adjusting the voltage applied to the detector.

According to another aspect of the invention, CPB mapping projection-optical systems are provided. Representative embodiments of such a system comprise an irradiation optical system, an E×B beam separator, an objective optical system, an imaging optical system, an adjustment-beam source, and an "evaluation chart." The irradiation optical system directs an irradiation charged particle beam along a first axis from an irradiation-beam source. The E×B beam separator is configured and situated to receive the irradiation beam from the irradiation optical system and to direct the irradiation beam downstream of the E×B beam separator. The objective optical system is configured and situated to receive the irradiation beam from the E×B beam separator, direct the irradiation beam to be incident on a specimen surface located at an object-surface plane downstream of the objective optical system, receive an observation charged particle beam generated by impingement of the irradiation beam on the specimen surface, and direct the observation beam to the E×B beam separator. The E×B beam separator causes the observation beam to propagate along a second axis having a direction different than the first axis. The imaging optical system is configured and situated to receive the observation beam from the E×B beam separator and to direct the observation beam from the E×B beam separator to a first detector. The adjustment-beam source is configured to emit an adjustment beam with respect to the object-surface so as to cause the adjustment beam to acquire data regarding a position of the object surface. The evaluation chart is configured so as to be insertable at the object-surface plane. The evaluation chart spontaneously emits an evaluation electron beam for evaluating an optical-performance characteristic of the imaging optical system. The evaluation electron beam desirably has a kinetic energy that is equal to the kinetic energy of the observation beam. Also, the evaluation electron beam desirably has an emission profile such as a dot-shaped profile, a line-shaped profile, or a planar profile.

The evaluation chart can comprise a hot-electron emitter. The evaluation chart is desirably disposed so that it can be inserted and removed at the position of the specimen surface. Such an evaluation chart spontaneously emits an evaluation electron beam for inspecting the optical performance of the mapping optical system. The kinetic energy of the evaluation beam is desirably equal to the kinetic energy of the observing beam.

It is also preferable for the emission profile of the evaluation beam to have any one of a dot shape, a line shape, or a plane shape.

The foregoing and additional features and advantages of the invention will be more readily apparent from the following detailed description, which proceeds with reference to the accompanying drawings.

DETAILED DESCRIPTION

Various aspects of the invention are exemplified in multiple representative embodiments, as described below.

Representative Embodiment 1

Figure 2:
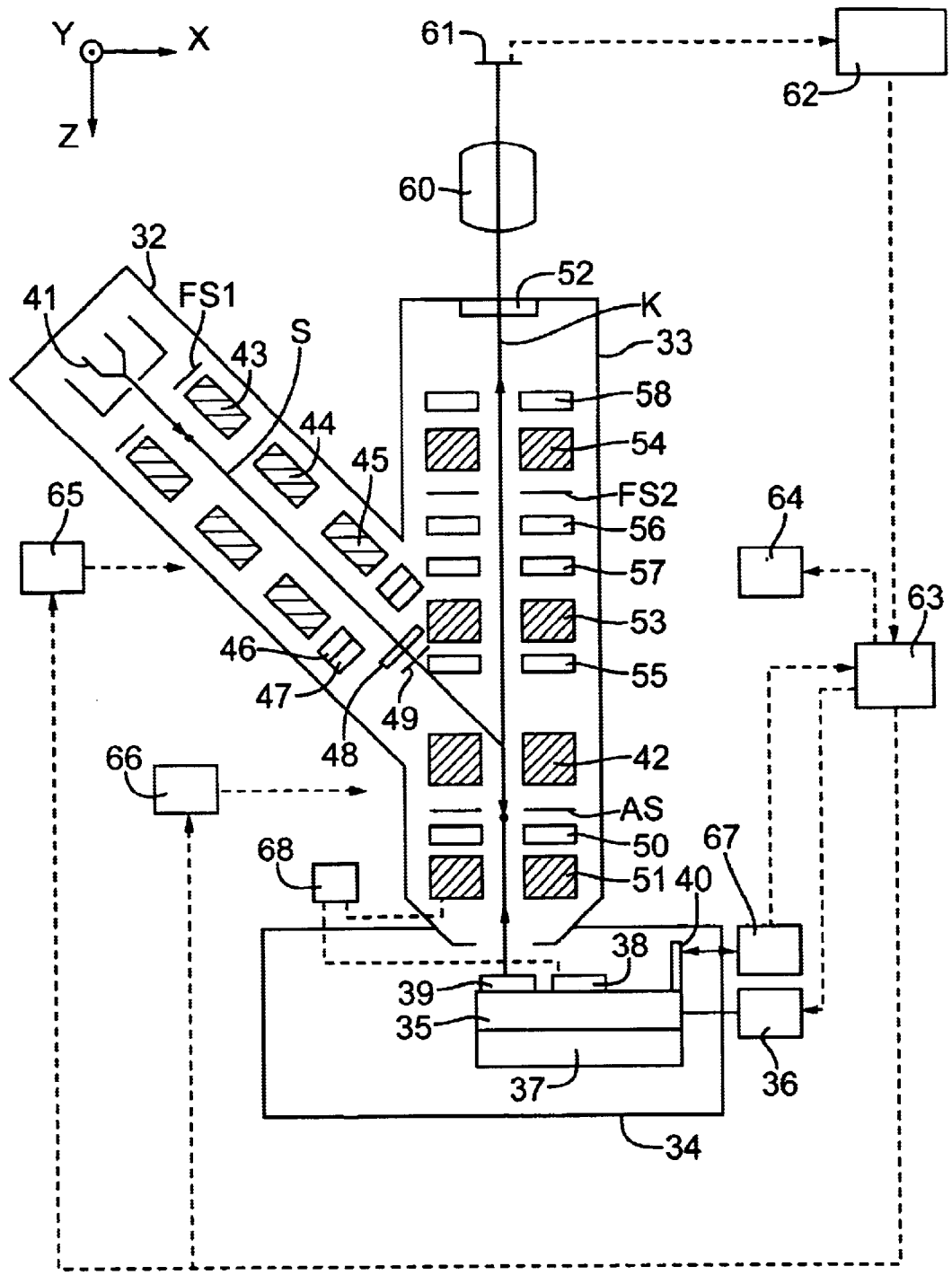
FIG. 2 is an elevational schematic drawing of Representative Embodiment 1 of a CPB mapping projection-optical system according to the invention.

A charged-particle-beam (CPB) mapping projection-optical system according to this embodiment is depicted in FIG. 2. Main subassemblies include a primary column 32, a secondary column 33, and a chamber 34. As can be discerned from the figure, each of the columns 32, 33 and the chamber 34 are in communication with each other and enclose a common space. The space is evacuated as required by a vacuum system (not shown) typically including a turbo-molecular pump.

The chamber 4 encloses an X stage 35 movable in the X direction by an X-stage driver 36 and a Y stage 37 movable in the Y direction by a Y-stage driver (not shown but understood to be configured similarly to the X-stage driver 36). Also inside the chamber 34 are a cold cathode 38 (serving in this embodiment as a source of an "adjustment beam" discussed below), a specimen 39, an X-movable mirror 40 and a Y-movable mirror (not shown but understood to be similar to the X-movable mirror 40) mounted on the X stage 37.

The cold cathode 38 is desirably a so-called "self-emitting beam source" that emits an electron beam (or other suitable charged particle beam) having a low kinetic energy (e.g., around 0.5 to 2 eV for electrons in this embodiment). Such a kinetic-energy level is near the value of the kinetic energy of a secondary electron beam K emitted from the object surface of the specimen 39, as described further below. The cold cathode 38 can be, e.g., a MOS-tunnel cold cathode, a Poly-Si/i-Si/n-Si cathode, a silicon field emitter, or analogous device. The cold cathode 38 can be fabricated by microlithography to form the requisite self-emitting pattern such as dots, lines-and-spaces, crosses, L-shapes, etc.

Turning now to the primary column 32, a primary beam S (also termed an "irradiation beam") is produced by an electron gun 41 (or other suitable CPB source). The primary beam S passes through a "primary optical system" (also termed an "irradiation optical system") and enters a Wien filter (also termed an "E×B" or "E×B beam separator") 42. The primary optical system in this embodiment comprises a field stop FS1, irradiation lenses 43, 44, 45; aligners 46, 47, a scanning aligner 48, and an aperture 49. The irradiation lenses 44, 45, 46 can be, e.g., electron lenses, circular lenses, quadrupole lenses, or octapole lenses.

The trajectory of the primary beam S is deflected by the Wien filter 42 which directs the primary beam to an aperture stop AS at which a crossover image of the electron gun 41 is formed. Passing through the aperture stop AS, the primary beam S then passes through a first aligner 50. The primary beam is then refracted by passage through a cathode lens 51 so as to illuminate the specimen 39 with Koehler illumination The aperture stop AS, aligner 50, and cathode lens 51 collectively comprise an "objective optical system."

As the specimen 39 is illuminated by the primary beam S, a secondary beam K and reflected electrons are produced. The distribution of charged particles in the secondary beam and in the reflected electrons corresponds with the surface shape, material distribution, and potential changes, etc., of the specimen 39. The secondary beam K primarily is used as an "observation beam" or "image-forming beam." As discussed above, the kinetic energy of the secondary beam K is "low" at around 0.5 to 2 eV in this embodiment.

The secondary beam K emitted from the specimen 39 sequentially returns through the cathode lens 51, the first aligner 50, the aperture stop AS, the Wien filter 42, and a "secondary optical system" (or "imaging optical system") as the secondary beam K propagates to a detector 52. The secondary optical system in this embodiment comprises a front imaging lens group 53, a rear imaging lens group 54, stigmators 55, 56, a second aligner 57, a third aligner 58, and a field stop F2. The field stop FS2 is in a conjugate relationship with the object surface of the specimen 39 about the cathode lens 51 and the front imaging lens group 53. The front imaging lens group 53 and the rear imaging lens group 54 of the secondary optical system can be electron lenses such as, e.g., circular lenses, quadrupole lenses, or octapole lenses.

The secondary beam K incident on the detection surface of the detector 52 is formed by the secondary optical system into an enlarged image of the specimen 39. The detector 52 desirably comprises an MCP (micro-channel plates) for amplifying incident electrons, a fluorescence plate for converting the electrons to light, and a vacuum window for emitting the converted light to the outside of the secondary column 33.

Light emitted from the detector 52 (i.e., an optical image of the specimen 39) is transmitted by a relay lens 60 to a pickup element 61 (e.g., a CCD or the like). The light incident to the pickup element 61 is converted thereby to a photoelectric signal that is transmitted to a controller 62. The controller 62 converts the photoelectric signal into an electrical signal that is routed to a CPU 63. The CPU 63 produces a corresponding video signal that is routed to a display 64 that displays an image of the specimen 39.

The CPU 63 also produces a control signal that is routed to a first power controller 65, a second power controller 66, and an electromagnetic-field controller (not shown in FIG. 2). The first power controller 65 controls electrical power applied to components in the primary optical system, the second power controller 66 controls electrical power applied to the cathode lens 51, the first aligner 50, and the secondary optical system. The electromagnetic-field controller controls the electromagnetic field generated by the Wien filter 42.

The CPU 63 also produces a control signal that is routed to the X-stage driver 36 and the Y-stage driver, and receives positional information about the stages 35, 37 from an X-interferometer 67 and a Y-interferometer (not shown, but understood to be configured similarly to the X-interferometer). Thus, multiple specimens can be sequentially observed and inspected.

Figure 3A:
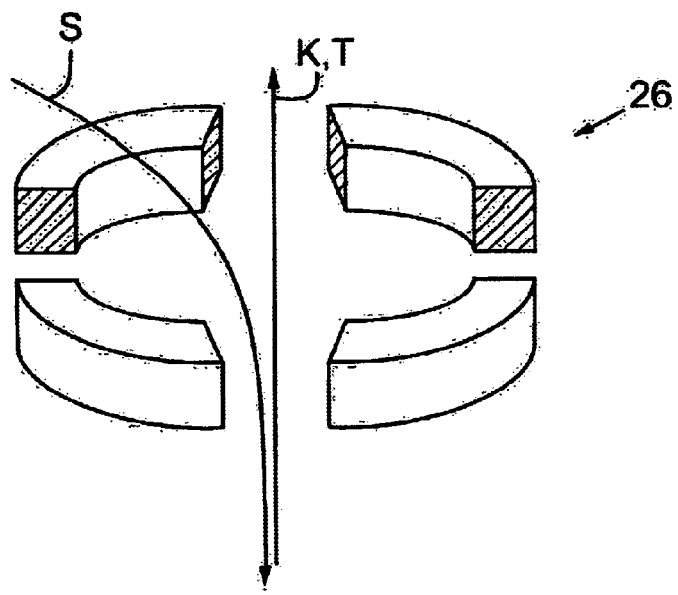
FIGS. 3(A)–3(C) are perspective views showing certain aspects of operation of the Wien filter (E×B beam separator) used in the CPB mapping projection-optical systems according to the invention.
Figure 3B:
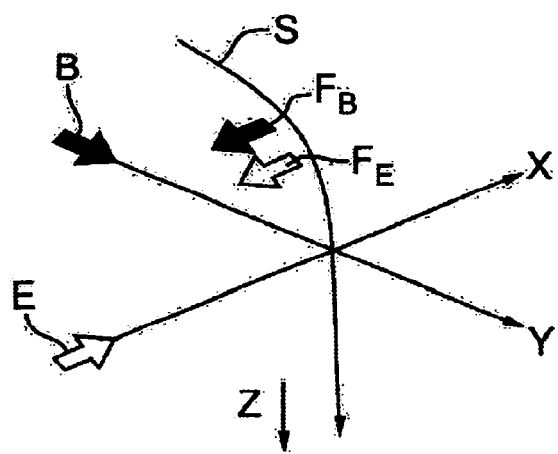
Figure 3C:
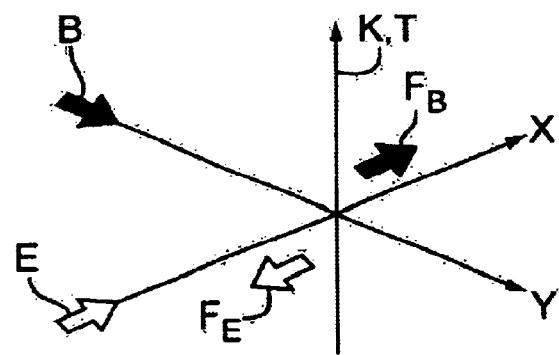

The Wien filter (E×B) 42 is now described in connection with FIGS. 3(A)–3(C). As shown in FIG. 3(A), the primary beam S emitted from the electron gun 41 is acted upon by the lens action of the primary optical system and thereby focused. Upon entering the Wien filter 42, the primary beam S experiences a deflection of its trajectory. The reason the trajectory is bent is because, as electrons in the primary beam S having a charge "q" proceed at velocity "v" in the +Z direction into the electrical field E and the magnetic field B (orthogonal to each other) produced by the Wien filter 42, the electrons are subjected to the resultant of the force $F_E$ (=qE) of the electrical field and the force $F_B$ (=−qvB) of the magnetic field, which are exerted in the −X direction. Thus, the trajectory of the primary beam S is bent within the XZ plane.

Meanwhile, the secondary beam K (produced as the specimen 39 is irradiated by the primary beam S) is acted upon by the lens action of the cathode lens 51. The secondary beam passes through the aperture stop AS situated at the focal position of the cathode lens 51 and enters the Wien filter 42. The secondary beam passes through the Wien filter 42 without experiencing any change in trajectory. The reason is shown in FIG. 3(C). As electrons in the secondary beam having a charge "q" proceed at a velocity "v" in the −Z direction into the orthogonal electrical and magnetic fields E, B, respectively, the electrons are subjected to the resultant of the force $F_E$ of the electrical field (which is exerted in the −X direction) and the force $F_B$ of the magnetic field (which is exerted in the +X direction). The respective absolute values of the force $F_E$ and the force $F_B$ are desirably set so that they are equal (i.e., E=vB) so that "Wien's condition" is fulfilled. Hence, the force $F_E$ and the force $F_B$ cancel each other out and consequently reduce to zero any force that would otherwise affect the secondary beam K. As a result, the secondary beam K proceeds straight through the Wien filter 42.

As described above, the Wien filter 42 has the function of a so-called electromagnetic prism, which selects the trajectory of a charged particle beam passing through it.

Adjustment of the CPB mapping projection-optical system according to this embodiment is described in connection with FIG. 4. For adjustment purposes, the cold cathode 38 is used to form a "dot" pattern. As an overall, "coarse" adjustment procedure, first the optical axis of the secondary optical system is aligned, then the electromagnetic field of the Wien filter 42 is adjusted, and then the optical axis of the primary optical system is adjusted using the dot pattern produced by the cold cathode 38.

Figure 4:
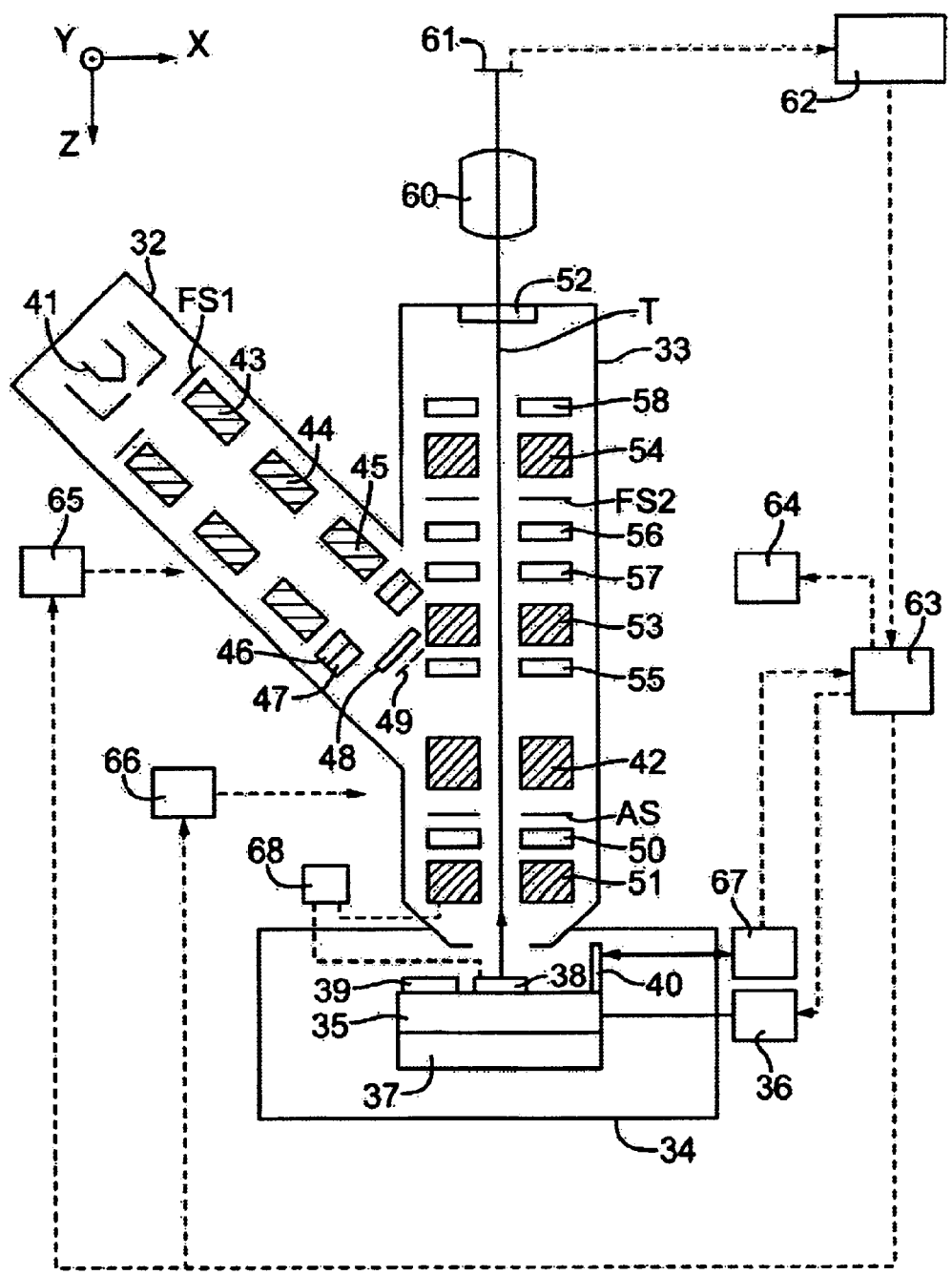
FIG. 4 is an elevational schematic drawing showing certain details of how the CPB mapping projection-optical system of the first representative embodiment is adjusted according to the invention.

As shown in FIG. 4, the cold cathode 38 is situated below the cathode lens 51. Next, the cathode lens 51 is energized by applying electrical energy thereto, while all other lenses are OFF. The cold cathode 38 produces an "adjustment beam T" that enters the cathode lens 51. In the cathode lens 51, the adjustment beam T is subjected to the electrical field produced by the cathode lens 51. After passing through the cathode lens 51, the adjustment beam T, similar to the secondary beam K described above, passes in sequence through the first aligner 50, the aperture stop AS, the Wien filter 42, and the secondary optical system. The adjustment beam then enters the detector 52.

Dot-pattern data carried by the adjustment beam T incident to the detector 14 (similar to the secondary beam K) is sequentially transferred to the relay lens 60, the pickup element 61, the controller 62, and the CPU 63. The resulting image of the dot pattern is displayed on the display 64.

Since no electrical power is being impressed at this time on lenses other than the cathode lens 51, the force to which the adjustment beam T is subjected by the time it reaches the detector 52 is only the electrical field produced by the cathode lens 51. In such a condition, the image of the dot pattern formed on the surface of the detector 52 is defocused by causing the voltage delivered to the cathode lens 51 to fluctuate in an AC fashion (thereby causing the cathode lens 51 to "wobble"). If the dot pattern is not aligned with the optical axis of the cathode lens 51, the image of the dot pattern on the display 64 will move (in response to the defocusing) within a plane that is perpendicular to the optical axis. The X stage 35 and the Y stage 37 are then shifted as required to cause the image of the dot pattern on the display 64 to remain stationary regardless of the defocusing. When the image of the dot pattern remains stationary on the display 64, the dot pattern is actually aligned with the optical axis of the cathode lens 51. This completes adjustment of the optical axis of the cathode lens 51.

Next, in addition to the cathode lens 51, electrical power is also applied to the front imaging lens group 53. The parameters of applied electrical energy are established such that an image of the dot pattern produced by the cold cathode 38 is formed on the detector 52. As with the adjustment of the cathode lens 51, the electrical power applied to the first aligner 50 is adjusted while the voltage applied to the front imaging lens group 53 is fluctuated in an AC fashion. Such adjustment continues until the image of the dot pattern as viewed on the display 64 no longer moves in response to the defocusing, at which time the optical axis of the front imaging lens group 53 is aligned with the optical axis of the cathode lens 51 adjusted previously.

Next, in addition to the cathode lens 51 and the front imaging lens group 53, electrical power is also applied to the rear imaging lens group 54. The power parameters are established such that an image of the dot pattern of the cold cathode 38 is formed on the detector 52. The electrical power applied to the second aligner 57 is adjusted while the voltage applied to the rear imaging lens group 54 is fluctuated in an AC fashion. Such adjustment continues until the image of the dot pattern as viewed on the display 64 no longer moves, at which time the optical axis of the rear imaging lens group 54 is aligned with the optical axis of the cathode lens 51 and of the front imaging lens group 53 adjusted previously.

Finally, the electrical power applied to the third aligner 58 is adjusted to move the image of the dot pattern to the center of the detector 52, thereby aligning the center of the detector 52 with the optical axis. Thus, the optical axes of the cathode lens 51 and the secondary optical system are aligned with each other.

Adjustment of the adjustment beam T can be accelerated by providing a potential difference between the cold cathode 38 and an electrode positioned object-wise of the cathode lens 51 by means of an acceleration power supply 68.

After adjusting the respective optical axes of the cathode lens 51 and the secondary optical system, as described above, the desired next step is to adjust the primary optical system and the Wien filter 42. At this time, Wien's condition for the Wien filter 42 and the secondary optical system is found so that the image of the dot pattern on the display 64 does not move even when power to the Wien filter 42 is turned ON and OFF.

Thus, in this embodiment, the illumination field of the primary optical system and the observation field of the secondary optical system are quickly and accurately aligned, yield an excellent video image as produced by the CPB optical system.

The optical axis of the secondary optical system was adjusted in this embodiment by forming a dot pattern in the cold cathode 38. Alternatively, aberrations can be similarly analyzed and corrected using a dot pattern by detecting the video image while defocusing the dot image or by using the intensity distribution of the dot image at the detector 52.

Spherical aberration in the secondary optical system can be corrected if a line-and-space pattern is used instead of a dot pattern for the pattern formed on the cold cathode 38. Distortion in the secondary optical system can be evaluated and corrected if a cross mark or an L-shaped mark is used.

Whereas a cold cathode 38 was used to produce the adjustment beam in this embodiment, an electron gun can alternatively be used for adjustment purposes. In any event, the emission profile of the adjustment-beam source at the object surface thereof is desirably at least one of a dot, a line, a cross, or an L-shape.

Whereas the trajectory of the primary beam S was bent by the Wien filter 42, and the secondary beam (as a representative charged particle beam) K proceeded in a straight path, the system can alternatively be configured so that the primary beam S proceeds straight and the trajectory of the secondary beam K is bent.

Whereas a CPB mapping projection-optical system was described above in which an electron beam was used, it will be understood that a CPB mapping projection-mapping system according to the invention can alternatively employ, e.g., an ion beam rather than an electron beam.

The CPB mapping projection-optical system according to this embodiment is a so-called "surface-to-surface" CPB mapping projection-optical system that illuminates an object surface using an electron beam from a beam source and forms an image thereof at an image surface. Such a system can be applied not only as a simple aperture for observation or inspection of a specimen, but also as an exposure apparatus for making semiconductor devices, or the like.

With this embodiment, as described above, since adjustment of the objective optical system and the imaging optical system each can be performed independently, using a self-emitting adjustment-beam source at the object surface, a CPB mapping projection-optical system and adjustment method are provided with which quick and accurate adjustments can be performed.

Representative Embodiment 2

Figure 5:
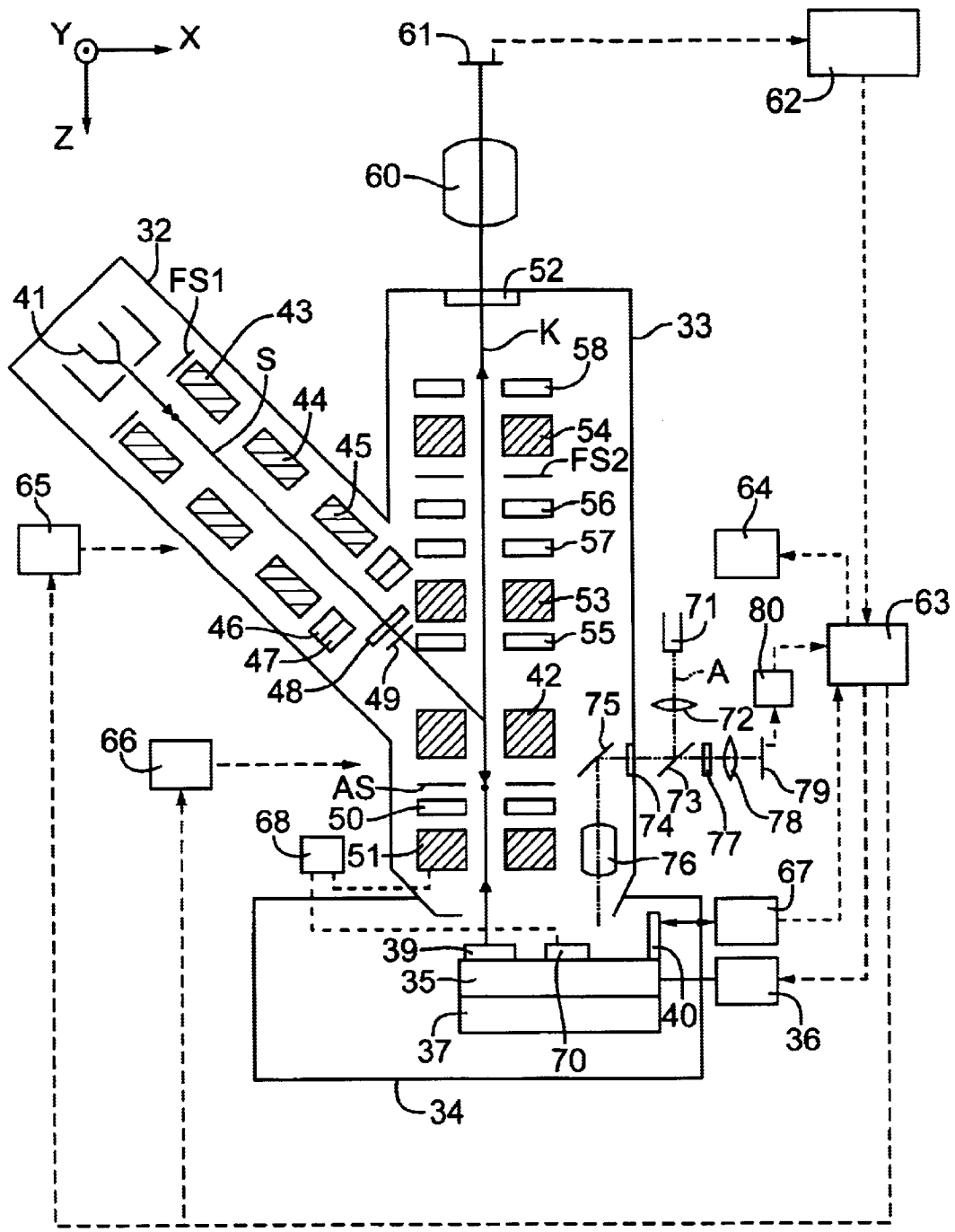
FIG. 5 is an elevational schematic drawing of Representative Embodiment 2 of a CPB mapping projection-optical system according to the invention.

With respect to this embodiment, reference is first made to FIG. 5 in which components that are similar to corresponding components in the first representative embodiment have the same reference designators. As in the first embodiment, the FIG. 5 embodiment comprises a primary column 32, a secondary column 33, and a chamber 34 all evacuated by a suitable vacuum system (not shown). Inside the chamber 34 are an X stage 35 (movable in the X direction by an X-stage driver 35) and a Y stage 37 (movable in the Y direction by a Y-stage driver, not shown). On the X stage 31 are mounted a "fiducial plate" 70, a specimen 39, an X-movable mirror 40, and a Y-movable mirror (not shown).

A primary beam S is produced by an electron gun 41 situated inside the primary column 32. The primary beam S passes through the "primary optical system" and enters the Wien filter (E×B) 42. The primary optical system comprises a field stop FS1, irradiation lenses 43–45, aligners 46–47, a scanning aligner 48, and an aperture 49. The irradiation lenses 43–45 are, e.g., electron lenses as described in the first representative embodiment.

The trajectory of the primary beam S is deflected by the Wien filter 42 toward the aperture stop AS at which a crossover image of the electron gun 41 is formed. After passing through the aperture stop AS, the primary beam S passes through a first aligner 50 and is then subjected to the lens action of a cathode lens 51. The primary beam then illuminates the specimen 39 with Koehler illumination.

As a result of the primary beam S irradiating the specimen 39, a secondary beam K and reflected electrons are produced. The secondary beam and the reflected electrons have respective distributions that correspond with the surface shape, material distribution, and potential changes exhibited by the specimen 39. Of these, the secondary beam K primarily is used as an observation beam. As discussed above, the kinetic energy of the secondary beam K in this embodiment is "low" at around 0.5 to 2 eV.

The secondary beam K emitted from the specimen 39 sequentially passes through the cathode lens 51, the first aligner 50, the aperture stop AS, the Wien filter 42, and a "secondary optical system." The secondary beam K then enters a detector 52. The secondary optical system comprises a front imaging lens group 53, a rear imaging lens group 54, stigmators 55–56, a second aligner 57, a third aligner 58, and a field stop FS2. The field stop FS2 is in a conjugate relationship with the object surface of the specimen 39 about the cathode lens 51 and the front imaging lens group 53. The front imaging lens group 53 and rear imaging lens group 54 are typically electron lenses, as discussed in the first representative embodiment.

The secondary electron beam K incident on the detection surface of the detector 52 is formed by the secondary optical system into an enlarged image of the specimen 39. The detector 52 in this embodiment desirably comprises an MCP (Micro-Channel Plate) for amplifying the incident electrons, a fluorescent plate for converting the electrons to light, and a vacuum window for emitting the converted light to the outside of the secondary column 33 (since the interior of the secondary column 33 is normally under a vacuum).

The light emitted from the detector 52, i.e., the optical image of the specimen 39, is transmitted by a relay lens 60 to a pickup element 61 such as a CCD or the like. The light incident to the pickup element 61 is converted to a photoelectric signal that is routed to a controller 62. The photoelectric signal routed to the controller 62 is converted into a corresponding electrical signal that is routed to a CPU 63 that produces a corresponding video signal delivered to a display 64 that displays the image of the specimen 39.

The CPU 63 also produces a control signal delivered to a first power controller 65, a second power controller 66, and an electromagnetic-field controller (not shown in the figure). The first power controller 65 controls the electrical energy applied to the components of the primary optical system; the second power controller 66 controls electrical energy applied to the cathode lens 51, the first aligner 50, and the secondary optical system; and the electromagnetic-field controller controls the electromagnetic field generated by the Wien filter 42.

The CPU 63 also generates respective control signals routed to the X-stage driver 36 and the Y-stage driver, and receives positional information about the X- and Y-stages from an X-interferometer 67 and a Y-interferometer (not shown), thereby allowing multiple specimens to be sequentially observed and inspected.

An off-axis optical system is configured as an optical microscope in this embodiment. An alignment light flux A exits an optical filter 71 or analogous appliance that delivers the alignment light flux A from a remote light source (not shown) such as a laser diode or the like. The alignment light flux A is converged by a lens 72 and enters a half-mirror 73. The alignment light flux A reflected by the half-mirror 73 enters a vacuum window 74. The vacuum window 74 is desirably a parallel plate to allow ready transmission of incoming and exiting light of the alignment light flux A into and out of, respectively, the secondary column 33 which is maintained under vacuum. Passing through the vacuum window 74, the alignment light flux A is reflected by a mirror 75 and is refracted by an objective lens 76 (including an aperture stop, not shown, at which an image is formed). After passing through the objective lens 76, the alignment light flux A illuminates the object surface on the X stage 35 with Koehler illumination.

The alignment light flux A reflected by the object surface returns through the objective lens 76, is reflected by the mirror 75, passes through the vacuum window 74, and is incident to the half-mirror 73. The returning alignment light flux A is transmitted by the half-mirror 73, passes through an index plate 77 and lens 78, and enters a CCD 79 on which an image of the object surface is formed. A photoelectric signal generated by the image on the CCD 79 is routed to a second controller 80 that converts the photoelectric signal into a corresponding electrical signal that is routed to the CPU 63.

Whereas video processing in this embodiment desirably encompasses processing and routing of signals from the CCD 79 in the off-axis optical system to the CPU 63, such processing can alternatively be performed by LSA (Laser Step Alignment) or LIA (Laser Interferometric Alignment), for example, commonly used in optical projection-exposure devices.

Whereas a half-mirror 73 desirably is used as a light splitter in this embodiment, a deflection beam splitter could alternatively be used instead, by way of example.

The Wien filter 42 is constructed and operates as described above in Representative Embodiment 1.

Figure 6:
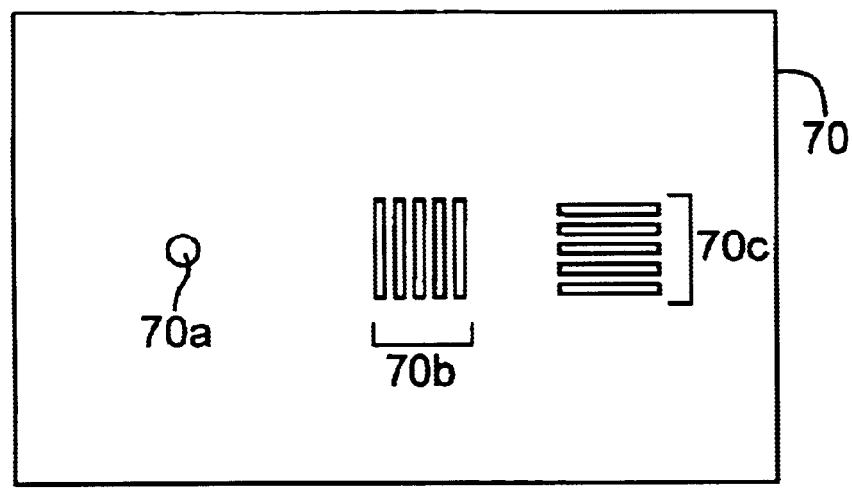
FIG. 6 is a plan view of an exemplary fiducial plate for use with the FIG. 5 embodiment.

An exemplary fiducial plate 70 is shown in FIG. 6, and defines a dot pattern 70a and line-and-space patterns 70b, 70c. The dot pattern 70a is a self-emitting pattern formed on a cold cathode by electron-beam microlithography. The dot pattern 70a can be, e.g., a circular pattern with a diameter of about 80 nm. The dot pattern 70a also serves as a source of the alignment beam T; i.e., the dot pattern 70a can serve as a fiducial mark for the CPB optical system.

A "cold cathode" is a self-emitting beam source that emits an electron beam having a low kinetic energy. The magnitude of the kinetic energy is at or near the magnitude of the kinetic energy of the secondary beam K emitted from the object surface of the specimen 39 described above. The cold cathode can be, e.g., a MOS-tunnel cold cathode, a poly-Si/i-Si/n-Si cathode, a silicon field emitter, or the like.

The line-and-space patterns 70b, 70c include, e.g., linear vertical and horizontal, respectively, features arrayed at equal intervals (e.g., 4 $\mu$m wide). The features are desirably defined in metal on a silicon substrate of the fiducial plate 70, and have a configuration similar to corresponding alignment marks on the specimen 39 formed using an optical projection-exposure device.

The relative positions of the dot pattern 70a and of the line-and-space patterns 70b, 70c are preferably known in advance.

Whereas, in this embodiment, the line-and-space patterns 70b, 70c are used as a fiducial mark for the off-axis optical system, other marks can be used for such a purpose so long as the marks are configured as a geometric pattern suitable for detection by the off-axis optical system. For example, the fiducial mark for the off-axis optical system can alternatively be any of various marks suitable for use with a CPB projection-optical system (e.g., as used as CPB projection microlithography). Further alternatively, the fiducial mark can be the dot pattern 70a formed on the cold cathode. In the latter instance, the line-and-space patterns 70b, 70c on the fiducial plate 70 would be unnecessary.

Figure 7:
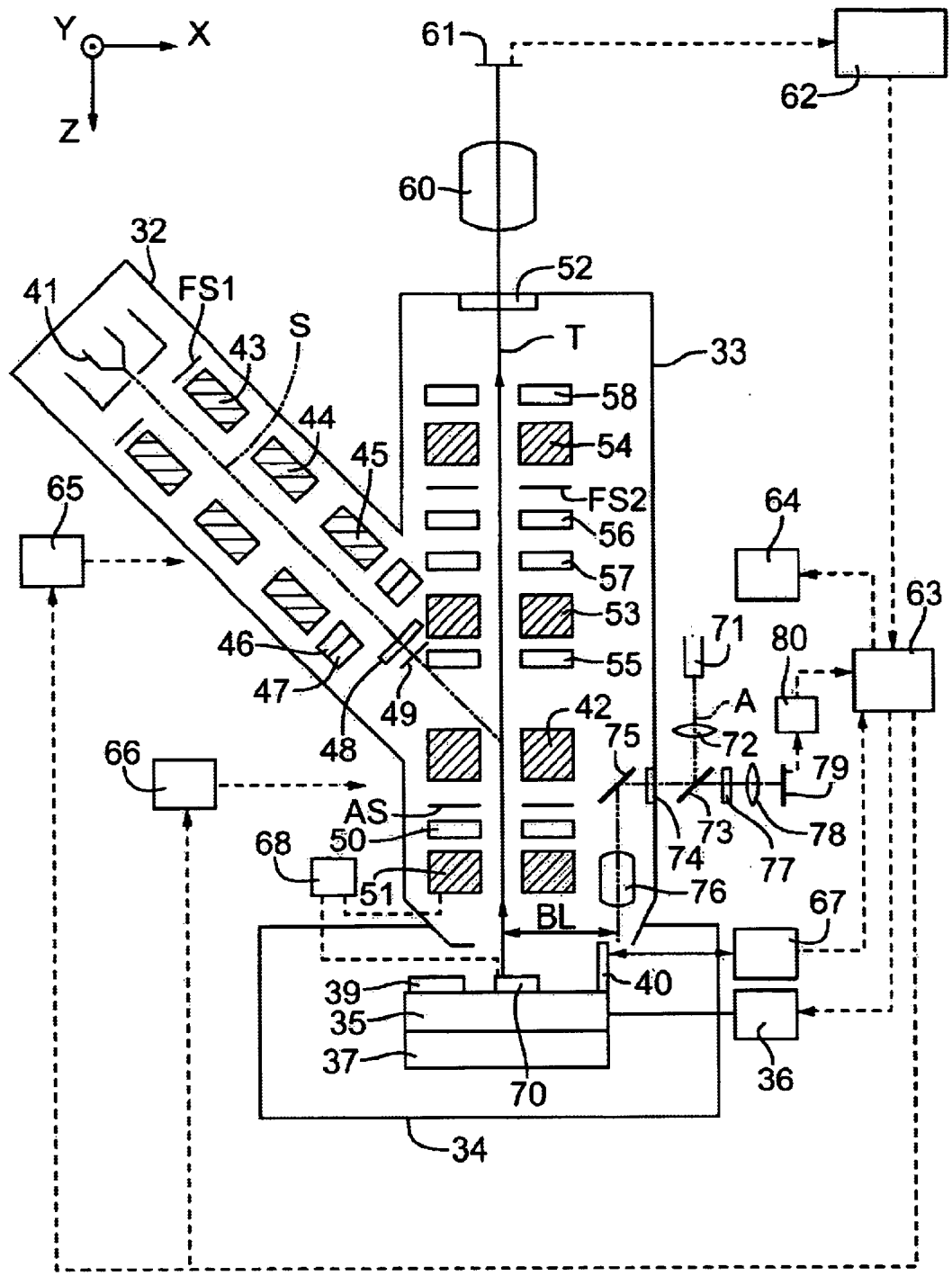
FIGS. 7 and 8 are elevational schematic drawings showing certain details of how the CPB mapping projection-optical system of the second representative embodiment is aligned, according to the invention, using a cold cathode.

Alignment of the CPB optical system using the cold cathode of this embodiment is described with reference to FIGS. 7 and 8. First, as shown in FIG. 7, the X stage 35 and the Y stage 37 are moved by means of the X-stage driver 36 and the Y-stage driver, respectively, to situate the dot pattern 70a on the fiducial plate 70 beneath the cathode lens 51 of the CPB optical system. Image information concerning the dot pattern 70a is obtained using the detector 52 that generates a corresponding signal that is routed to the CPU 63. Meanwhile, stage-position data as obtained by the X-interferometer 67 and the Y-interferometer are routed to the X-stage driver 36 and the Y-stage driver. Based on such information, the position of the dot pattern 70a is adjusted so as to place the dot pattern 70a in accurate alignment with the optical axis of the CPB optical system.

Figure 8:
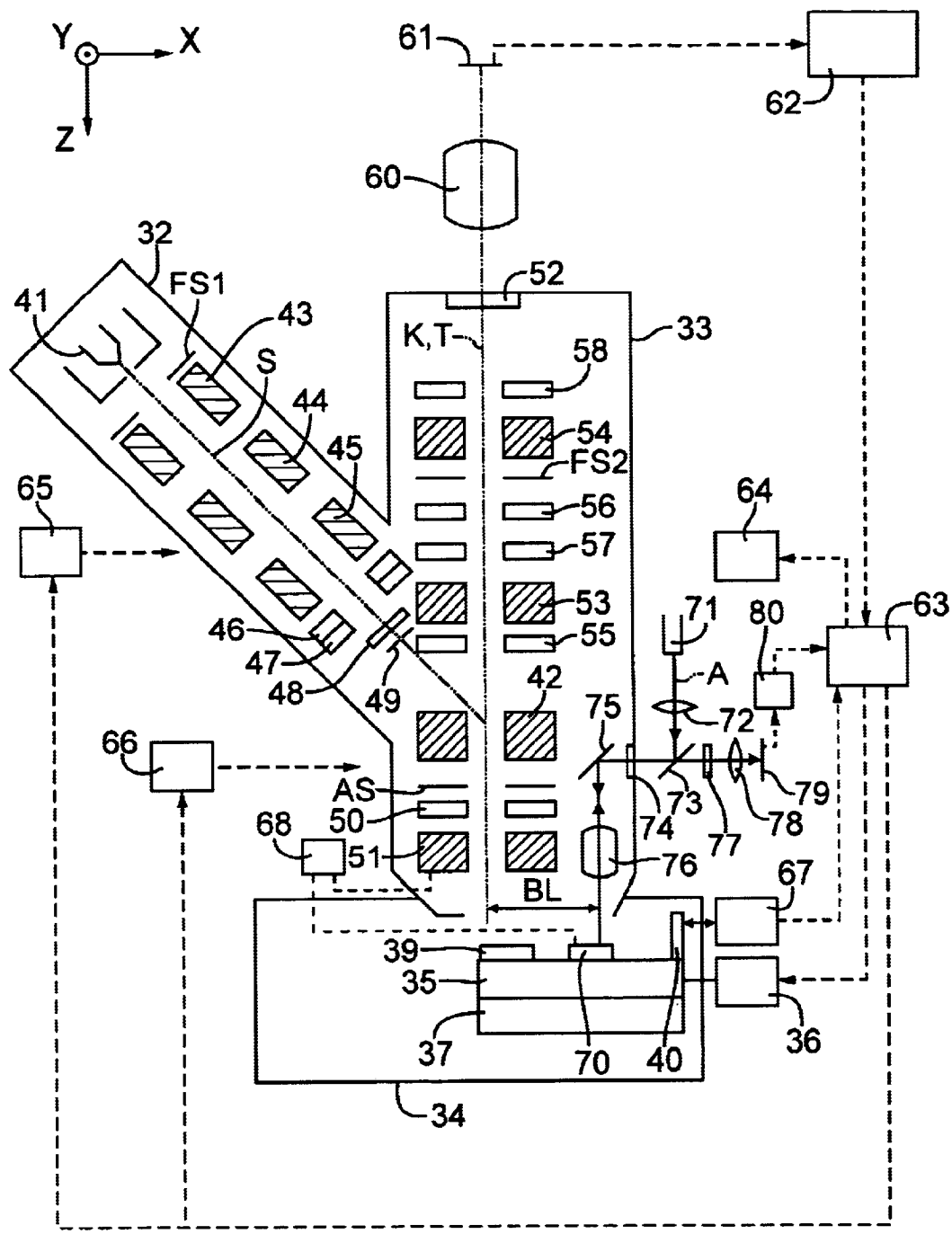

Next, as shown in FIG. 8, the X stage 35 and the Y stage 37 are moved so as to situate the line-and-space patterns 70b, 70c beneath the objective lens 76 of the off-axis optical system. Image data concerning the line-and-space patterns 70b, 70c are detected by the CCD 79 that generates corresponding signals that are routed to the CPU 63. Meanwhile, stage-position data obtained by the X-interferometer 67 and the Y-interferometer are routed to the X-stage driver 36 and Y-stage driver, respectively. The positions of the line-and-space patterns 70b, 70c are adjusted so as to be accurately aligned with corresponding patterns defined on the index plate 77 in the off-axis optical system.

Since the relative position relationships of the dot pattern 70a with the line-and-space patterns 70b, 70c are known in advance, the distance between the optical axis of the CPB optical system and the optical axis of the off-axis optical system, i.e., the so-called "baseline" BL, is found by executing the procedure described above.

After the baseline BL has been determined, the X stage 35 and the Y stage 37 are moved, thereby situating the specimen 39 beneath the objective lens 76 of the off-axis optical system. Data concerning the image of the alignment marks on the specimen 39 (as detected by the CCD 79 and routed to the CPU 63) and stage-position information (as detected by the X-interferometer 67 and the Y interferometer and routed to the CPU 63) are fed back to the X-stage driver 36 and the Y-stage driver. Thus, the alignment marks on the specimen 39 are aligned with the pattern on the index plate 77 in the off-axis optical system.

The position of the specimen 39 on the X stage 35 is checked at this time because the relative positional relationship between the specimen 39 and the alignment marks on the specimen 39 is already known. Finally, the X stage 35 and the Y stage 37 are moved according to the baseline BL previously determined so as to situate the specimen 39 at the irradiation position of the CPB optical system. Then, the specimen 39 can be observed and inspected.

Since the respective optimum fiducial marks can be selected for the CPB optical system and the off-axis optical system using this embodiment, as described above, it is possible to accurately and quickly observe and inspect the specimen 39.

Whereas the fiducial mark for the off-axis optical system in this embodiment is desirably defined as a geometric pattern (e.g., line-and-space patterns 70b, 70c, formed on the fiducial plate 70), a suitable alternative is, e.g., a surface-emitting laser that forms a geometric pattern. In the alternative situation, the illumination system shown in FIG. 7 (i.e., the light source, optical fiber 71, lens 72, and half-mirror 73) would be unnecessary.

By increasing its imaging magnification, the off-axis optical system of this embodiment can be used not only as a simple alignment microscope but also as a viewing microscope.

Representative Embodiment 3

Figure 9:
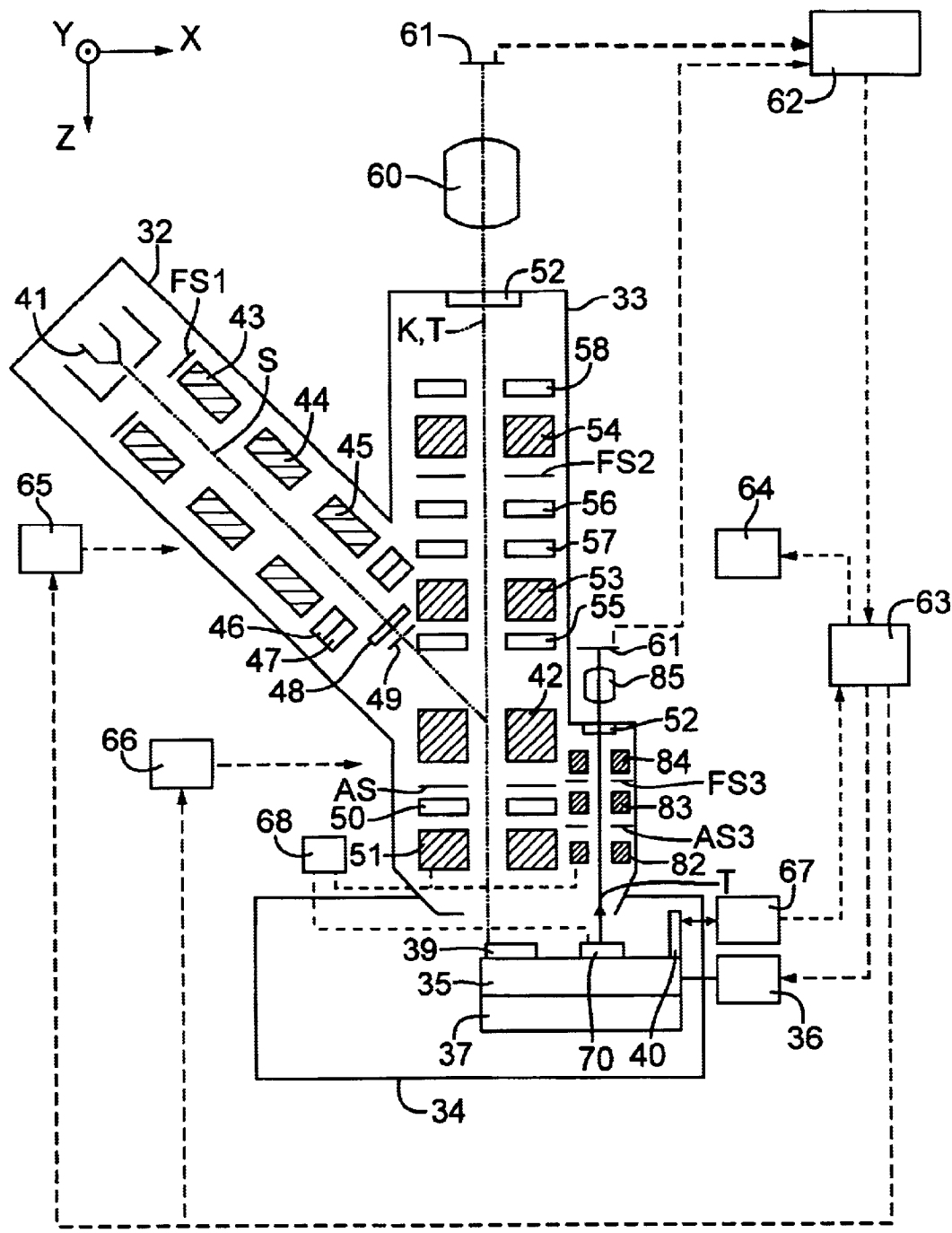
FIG. 9 is an elevational schematic drawing of Representative Embodiment 3 of a CPB mapping projection-optical system according to the invention.

This embodiment is shown in FIG. 9, schematically depicting the CPB optical system of this embodiment. In this embodiment, a mapping electron microscope is used instead of the optical microscope in Representative Embodiment 2. A dot pattern 70a is formed on a cold cathode on the fiducial plate 70 (see preceding embodiment) and is used as a common fiducial mark for the CPB optical system and for the off-axis optical system.

In FIG. 9, components that are the same as in the second representative embodiment have the same reference designators and are not described further.

An alignment beam T emitted from the dot pattern 70a sequentially passes through a cathode lens 82 and an imaging optical system to the detector 52. The imaging optical system, like the secondary optical system in the CPB optical system, comprises an aperture stop AS3, a front imaging lens group 83, a field stop FS3, and a rear imaging lens group 84.

The alignment beam T incident to the detector 52 forms an image of the dot pattern 70a by means of the imaging optical system. The image of the dot pattern 70a is converted by the detector 52 into a corresponding optical image. The optical image passes through a relay lens 85 and enters a pickup element 61. Light incident to the pickup element 61 is converted into a corresponding photoelectric signal that is routed to a first controller 62. The first controller 62 converts the photoelectric signal into a corresponding electrical signal that is routed to the CPU 63.

As data concerning the dot pattern 70a detected by the pickup element 41 is routed to the CPU 63, stage-position data obtained by the X-interferometer 67 and the Y-interferometer are routed back to the X-stage driver 36 and the Y-stage driver. Responsive to such feedback, the position of the dot pattern 70a is thus adjusted to accurately align with the optical axis of the off-axis optical system.

The baseline BL is found and the specimen 39 is observed and inspected in the same manner as described in the second representative embodiment.

This embodiment allows respective optimum fiducial marks to be selected for the CPB optical system and the off-axis optical system. Hence, this embodiment allows the specimen 39 to be accurately and quickly observed and inspected.

Whereas a mapping electron microscope was used as the off-axis optical system in this embodiment, a scanning electron microscope, for example, can alternatively be used. Alignment and review can be performed, with this embodiment, in a manner similar to the second representative embodiment. When performing such review, high magnification easily can be obtained if a scanning electron microscope were used as the off-axis optical system.

Whereas a dot pattern 70a on the fiducial plate 70 is desirably used as the fiducial mark for the CPB optical system in this embodiment, a line-and-space pattern, a cross pattern, or an L-shaped mark alternatively can be used to advantage.

In this and the preceding embodiment, the positions of the CPB optical system and the off-axis optical system are desirably stationary, with the specimen 39 and the fiducial plate 70 being moved relative to the CPB optical system and the off-axis optical system by moving the X stage 35 and the Y stage 37. Alternatively, the X stage 35 and the Y stage 37 can be held stationary while the CPB optical system and off-axis optical system are moved.

Whereas the trajectory of the primary beam S was bent by a Wien filter (ExB) 42, and whereas the secondary beam K proceeded straight through the Wien filter 42, this embodiment can alternatively be configured such that the primary beam S proceeds straight through the Wien filter 42 and the trajectory of the secondary beam K is bent.

Whereas an electron beam was utilized in each of this and the preceding embodiments, it will be understood that another type of charged particle beam, such as an ion beam, can alternatively be used.

A CPB optical system according to either this or the preceding embodiment easily can be applied to microlithographic projection-exposure equipment and the like for use in manufacturing semiconductor devices, in addition to stand-alone observation apparatus or inspection apparatus.

Representative Embodiment 4

In this embodiment of a CPB mapping projection-optical system, as in the first representative embodiment, the primary optical system, the secondary optical system, and the cathode lens can be adjusted independently of each other by use of a self-emitting adjustment-beam source, such as a cold cathode, on or near the specimen surface.

Figure 10:
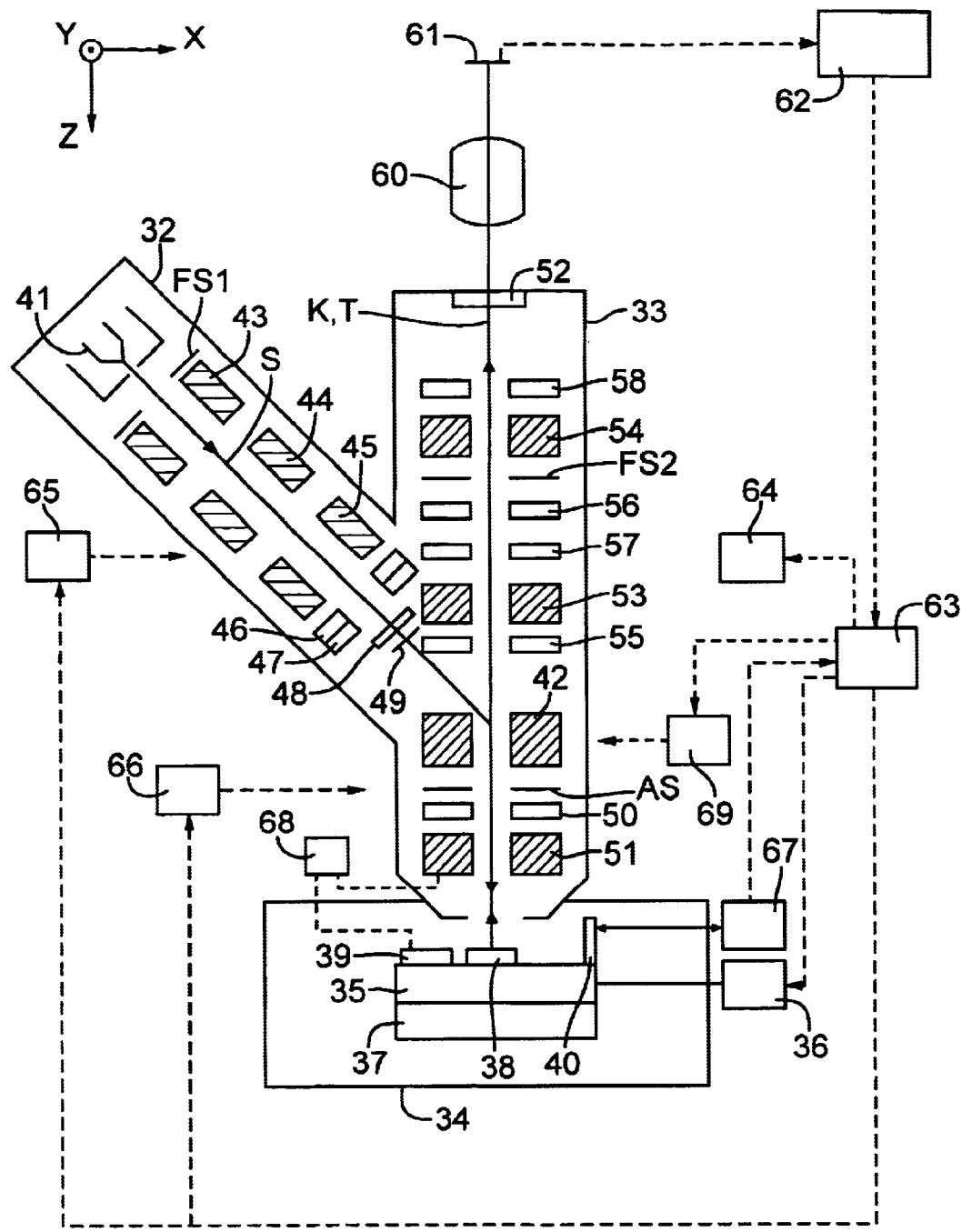
FIG. 10 is an elevational schematic drawing of Representative Embodiment 4 of a CPB mapping projection-optical system according to the invention.

This embodiment is depicted schematically in FIG. 10, in which components that are the same as in the preceding embodiments have the same reference designators and are not described further.

The cold cathode 38 used in this embodiment is desirably a so-called "self-emitting" beam source that emits an electron beam having a low kinetic energy (peak energy is generally 10 eV or less in this embodiment). The magnitude of the kinetic energy is at or near the magnitude of the kinetic energy of the secondary beam K (generally less than 10 eV in this embodiment) emitted from the object surface of the specimen 39, as previously described.

The CPU 63 in this embodiment generates a control signal that is routed to the first power controller 65, a second power controller 66, and an electromagnetic-field controller 69. The first power controller 65 controls electrical energy applied to respective components in the primary optical system; the second power controller 66 controls the respective electric energies applied to the cathode lens 51, the first aligner 50, and components in the secondary optical system; and the electromagnetic-field controller 69 controls the electromagnetic field generated within the Wien filter (ExB) 42 by controlling the voltage and current applied to the Wien filter 42. In addition, the respective electrical energy applied to these various components can be selectively turned ON and OFF by external commands from the operator or other suitable means.

The method for adjusting a CPB mapping projection-optical system according to this embodiment is now described. For such a purpose, the cold cathode 38 desirably forms a dot pattern. First, the optical axis of the secondary optical system is adjusted using the dot pattern of the cold cathode 38. In FIG. 10, the X stage 35 and the Y stage 37 are actuated to move by the respective X-stage driver 36 and the Y-stage driver (not shown) so as to situate the cold cathode 38 beneath the cathode lens 51. Next, the cathode lens 51 is energized (i.e., a voltage is impressed on the cathode lens 51) while the other lenses are turned OFF. The adjustment beam T emitted from the cold cathode 38 enters the cathode lens 51. As it passes through the cathode lens 51, the adjustment beam T is subjected to the electrical field generated by the cathode lens 51. After passing through the cathode lens 51, the adjustment beam T, like the secondary beam K, passes sequentially through the first aligner 50, the aperture stop AS, the Wien filter 42, and the secondary optical system. The adjustment beam T then enters the detector 52.

Data generated by the detector 52 as the detector receives the adjustment beam T are sequentially routed to the relay lens 60, the pickup element 61, the first controller 62, and the CPU 63. The CPU generates a corresponding signal that is routed to the display 64 that displays a corresponding video image of the dot pattern.

Since, at this step in the procedure, no electrical energy is being applied to any lens other than the cathode lens 51, the only force to which the adjustment beam T is subjected as it propagates to the detector 52 is the electrical field in the cathode lens 51. The image of the dot pattern on the detector surface of the detector 52 is defocused by causing the voltage of the cathode lens 51 to fluctuate in an AC fashion ("wobble"). If the dot pattern is not on the optical axis of the cathode lens 51, then the image of the dot pattern on the display 64 will move within a plane perpendicular to the optical axis together with the defocusing. The X stage 35 and the Y stage 37 are adjustably shifted until the image of the dot pattern on the display 64 no longer moves, regardless of defocusing. The position of the dot pattern at which no motion is evident on the display 64 is the position at which the dot pattern is on the optical axis of the cathode lens 51. This completes adjustment of the optical axis of the cathode lens 51.

Next, electrical energy is applied also to the front imaging lens group 53 as well as on the cathode lens 51. At this time, the parameters of applied electrical energy are established so that the image of the dot pattern of the cold cathode 38 is formed on the detector 52; as with the adjustment of the optical axis of the cathode lens 51, the electrical energy applied to the first aligner 50 is adjusted, while fluctuating the voltage in an AC fashion, until the displayed image of the dot pattern no longer moves. Thus, the optical axis of the front imaging lens group 53 is aligned with the optical axis of the cathode lens 51.

Next, in addition to the cathode lens 51 and front imaging lens group 53, electrical energy is also applied to the rear imaging lens group 54. At this time, the parameters of applied electrical energy are established so that the image of the dot pattern of the cold cathode 38 is formed on the detector 52. The electrical energy applied to the second aligner 57 is adjusted, while fluctuating the voltage in an AC fashion, until the displayed image of the dot pattern no longer moves. Thus, the optical axis of the rear imaging lens group 54 is aligned with the optical axis of the cathode lens 51 and front imaging lens group 53.

Finally, the electrical energy applied to the third aligner 58 is adjusted to move the image of the dot pattern to the center of the detector 52 to permit alignment of the center of the detector 52 with the optical axis. Thus, the optical axes of the cathode lens 51 and of the secondary optical system are aligned with each other.

The adjustment beam T can be accelerated by providing a potential difference between the cold cathode 38 and an electrode positioned object-wise of the cathode lens 51 by means of an acceleration power supply 68.

Whereas the optical axis of the secondary optical system was adjusted in this embodiment by forming a dot pattern on the cold cathode 38, various aberrations can be analyzed similarly using a dot pattern. This is performed by detecting a video image of a defocused dot-pattern image or obtaining an intensity distribution of the dot-pattern image at the detector 52.

Spherical aberration in the secondary optical system can be measured and corrected by using a line-and-space pattern rather than a dot pattern on the cold cathode 38. Distortion in the secondary optical system can be measured and corrected by using a cross mark or an L-shaped mark on the cold cathode 38.

After the optical axes of the cathode lens 51 and the secondary optical system have been adjusted, the electron gun 41 and primary optical system can be adjusted using steps similar to those described above. After the electron gun 41 and primary optical system have been adjusted, the Wien's condition of the Wien filter 42 can be adjusted. As discussed above, the Wien's condition is the condition under which the primary bean S is deflected at a desired angle as the primary beam passes through the Wien filter 42, while the secondary beam K proceeds straight through the Wien filter 42.

The Wien's condition of the Wien filter 42 can be adjusted using the cold cathode 38. To such end, in FIG. 10, the cold cathode 38 is situated beneath the cathode lens 51 by moving the X stage 35 and the Y stage 37 using the X-stage driver 36 and Y-stage driver, respectively.

The Wien's condition of the Wien filter 42 relative to the secondary optical system, i.e., the condition under which the secondary beam K proceeds straight through the Wien filter 42, is found by turning the voltage and current applied to the Wien filter 42 ON and OFF. Typically, the voltage and current applied to the Wien filter 42 are set so that the position of the dot-pattern image of the cold cathode 38 observed on the display 64 when voltage and current are not being applied to the Wien filter 42 is aligned with the position of the image of the cold cathode 38 when voltage and current are being applied to the Wien filter.

Finally, a fine adjustment can be performed using the aligners 46, 47 so that the optical axis of the secondary optical system and the optical axis of the primary optical system are aligned with each other between the Wien filter 42 and the specimen 39 whenever the set voltage and current are applied to the Wien filter 42.

Thus, with this embodiment, the Wien's condition of the Wien filter 42 can be adjusted easily. In this way, the illumination field of the primary optical system and the observation field of the secondary optical system are quickly and accurately aligned with each other, allowing an excellent video image to be obtained from the CPB optical system.

Whenever a voltage and current are applied to the Wien filter 42, aberrations such as astigmatism and the like normally are produced in the secondary optical system. Consequently, it is desirable also to adjust the stigmators 55, 56 (to provide correction of such aberrations) at the same time the Wien's condition is set. Thus, imaging parameters can be maintained linking the lens action produced at this time and lens conditions in the secondary optical system. Typically, the respective voltage and current applied to the Wien filter 42 as well as the electrical energy applied to the stigmators 55, 56, the cathode lens 51, the front imaging lens group 53, and the rear imaging lens group 54 are simultaneously adjusted so that the position of the cold cathode 38 image on the display 64 does not fluctuate, regardless of whether power applied to the Wien filter 42 is ON or OFF.

Whereas, in this embodiment, the trajectory of the primary beam S is bent by the Wien filter 42 while the secondary beam K proceeds in a straight path through the Wien filter, the system alternatively can be configured such that the primary beam S proceeds straight and the trajectory of the secondary beam K is bent.

Whereas an electron beam is used as the charged particle beam in this embodiment, any of various other charged particle beams (e.g., ion beam) can alternatively be used.

Whereas a cold cathode 38 is used in this embodiment as the source of the adjustment beam, a separate electron gun alternatively can be used.

Whereas the adjustment order in this embodiment proceeds first with the cathode lens 51, then the secondary optical system, then the primary optical system, and then the Wien filter 42, the order can be changed, if desired, to achieve the same goal. An exemplary alternative order is adjusting the cathode lens 51 first, then adjusting the primary optical system, then the secondary optical system, and then the Wien filter 42.

The CPB optical system of this embodiment is a so-called "surface-to-surface" CPB optical system that illuminates the surface of the specimen 39 using an electron beam from a beam source and forms an image thereof at an imaging surface. However, this CPB optical system also can be utilized as a semiconductor exposure device, or the like.

Representative Embodiment 5

This embodiment is mainly directed to evaluation charts for use with a mapping CPB microscope such as any of the embodiments described above. Evaluation charts according to this embodiment do not require adjustment of the optical axis of the illumination optical system. Also, evaluation charts according to this embodiment exhibit a stable distribution of kinetic energy of an electron beam emitted from the evaluation chart.

In a mapping CPB microscope such as according to any of the preceding embodiments, it will be recalled that a "primary beam" (or "irradiation beam") S passing through a "primary optical system" (or "irradiation optical system") irradiates the surface of the specimen 39. Such irradiation of the specimen 39 generates a "secondary beam" (or "observation beam") K that passes through a "secondary optical system" (or "mapping optical system") to form an image of the irradiated surface. An evaluation chart according to this embodiment is especially adapted to be placed at the position of the specimen 39. The evaluation chart emits an "evaluation beam" E used for evaluating and adjusting the secondary optical system.

For such purposes, it is desirable that the kinetic energy of the inspection beam E be essentially equal to the kinetic energy of the secondary beam K. It is also desirable that the emission profile of the evaluation beam E have any of a dot profile, line profile, or plane profile.

Figure 11:
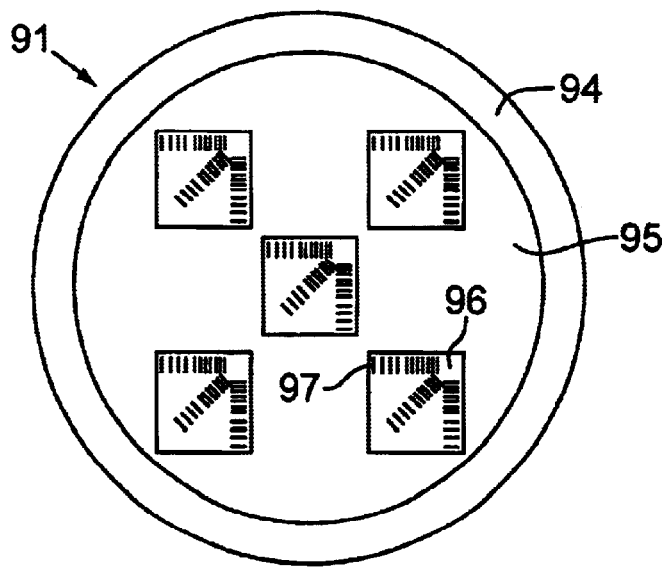
FIG. 11 is a plan view of an elevational chart according to Representative Embodiment 5 of the invention.
Figure 12:
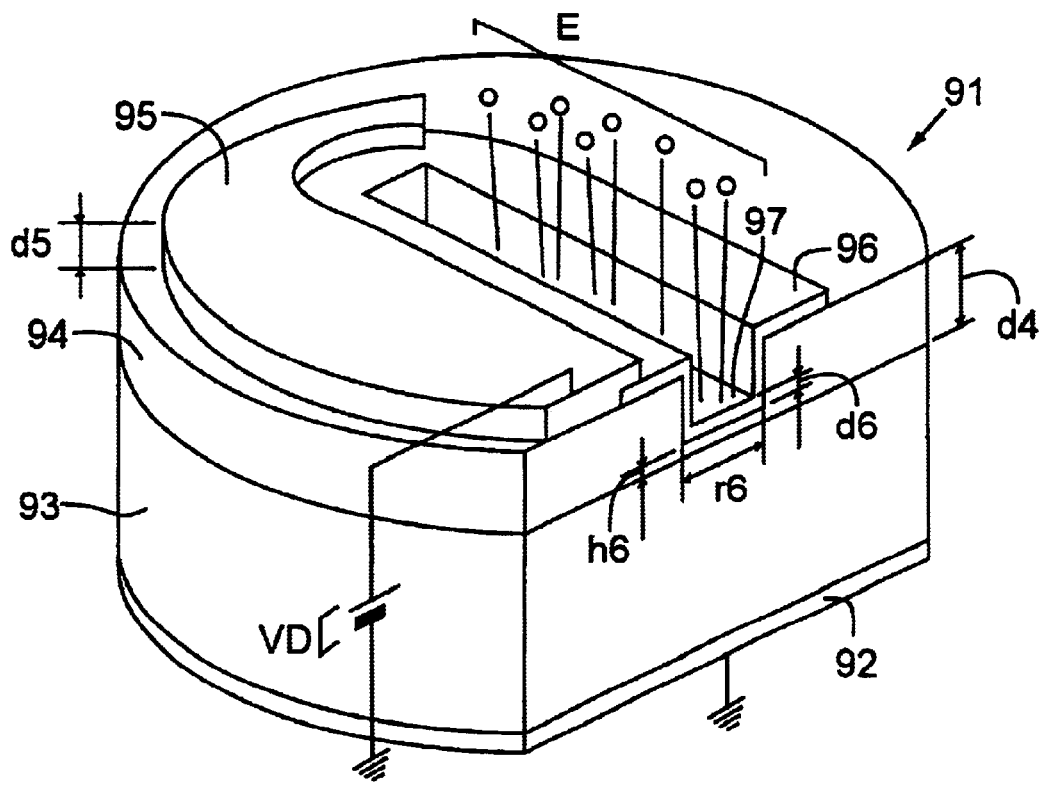
FIG. 12 is a perspective view showing certain internal details of the hot-electron emitter 91 shown in FIG. 11.

The evaluation chart can be formed on a hot-electron emitter, as shown for example in FIGS. 11 and 12.

The FIG. 11 configuration is an evaluation chart situated on a hot-electron emitter 91. A gate electrode 95 (desirably made of aluminum Al) and an $n^+$-Si layer 96 are formed on the surface of the hot-electron emitter 91. Multiple arrays of emitting line features 97 are formed on the $n^+$-Si layer 96. The pitch of each array of line features 97 changes step-wise in a meridional direction and in a sagittal direction. The pitch of the line features 97 ranges from approximately 100 nm to several $\mu$m in this embodiment.

Each line feature 97 spontaneously emits an electron beam, which collectively constitute the evaluation beam E. In other words, each individual line feature 97 corresponds with an electron-emission surface of the hot-electron emitter 91. The size and pitch of the line features 97 can be made as small as, e.g., several tens of nanometers. (Such resolution is obtainable by electron-beam microlithography.)

The evaluation chart of FIG. 11 is disposed at the position of the specimen surface in a CPB mapping microscope as described above, and used to determine the resolution of the mapping optical system.

In normal use of a CPB mapping microscope for observation of a specimen, either the specimen 39 is grounded or the specimen is maintained at a constant potential. Hence, it is desirable with the hot-electron emitter 91 to completely cover the surface of the evaluation chart with the gate electrode 95 or with another surficial metallic film to facilitate maintaining a predetermined potential. By either grounding the gate electrode 95 or maintaining it at a constant potential, actual observation conditions are reproduced during use of the evaluation chart.

A representative internal structure of the hot-electron emitter 91 is shown in FIG. 12, which is an oblique perspective view of one of the line features 97 of the evaluation chart of FIG. 11 with part of the perimeter sectioned. A rear electrode 92 (desirably made of aluminum)

is formed on the rear surface of a silicon (Si) substrate 93. The rear electrode 92 is desirably grounded during use. An insulating layer 94 (desirably made of SiO$_2$) is formed on the upper surface of the substrate 93. By way of example, the thickness d4 of the insulating layer 94 is, e.g., 500 nm. A groove having a width "r6" of, e.g., 100 nm is formed by electron-beam microlithography in the insulating layer 94. Also by way of example, the thickness of the remaining insulating layer, i.e., the dimension "h6" between the groove and the upper surface of the substrate 93, is 10 nm. The n$^+$-Si layer 96, having an exemplary thickness "d6" of 20 nm, is formed on top of the groove. The gate electrode 95 is formed over the insulating layer 94, leaving only the opening of the groove in the n$^+$-Si layer 96. Whenever a bias voltage is applied to the gate electrode 95 by a power supply VD, an evaluation electron beam E is emitted from the groove. The evaluation electron beam E has a transverse profile corresponding with the shape of the opening of the groove (i.e., the beam E has a transverse profile corresponding with the shape of the line feature 97). The distribution of the emitted electrons in the evaluation beam E can be adjusted by changing the thickness h6 of the insulating layer 94 or by changing the voltage applied to the gate electrode 95.

The evaluation chart of FIGS. 11 and 12, as described above, is a so-called "self-emitting" evaluation chart. For use in measuring and adjusting the performance of primary and secondary optical systems (as described generally in the preceding embodiments), the hot-electron emitter 91 is placed at the position of the specimen 39. Thus, the resolution of the primary and second optical systems can be measured and adjusted without having to use the primary optical system to produce a primary beam. In addition, image distortion produced by the secondary optical system can be evaluated by measuring the amount of distortion, of the line-feature pattern over the entire surface of the evaluation chart, produced by the secondary optical system alone.

Whereas an evaluation chart comprising the line features 97 is used in this embodiment for evaluating and adjusting the optical performance of a CPB mapping microscope, the optical axis of the secondary optical system can be adjusted if a dot pattern were to be used as the inspection chart (as described in the preceding embodiments). Further alternatively, various aberrations in the mapping optical system can be evaluated using a planar pattern, such as a cross pattern or a pattern of L-shaped features. If required, a composite chart can be used in which variously shaped features are used.

Figure 1:
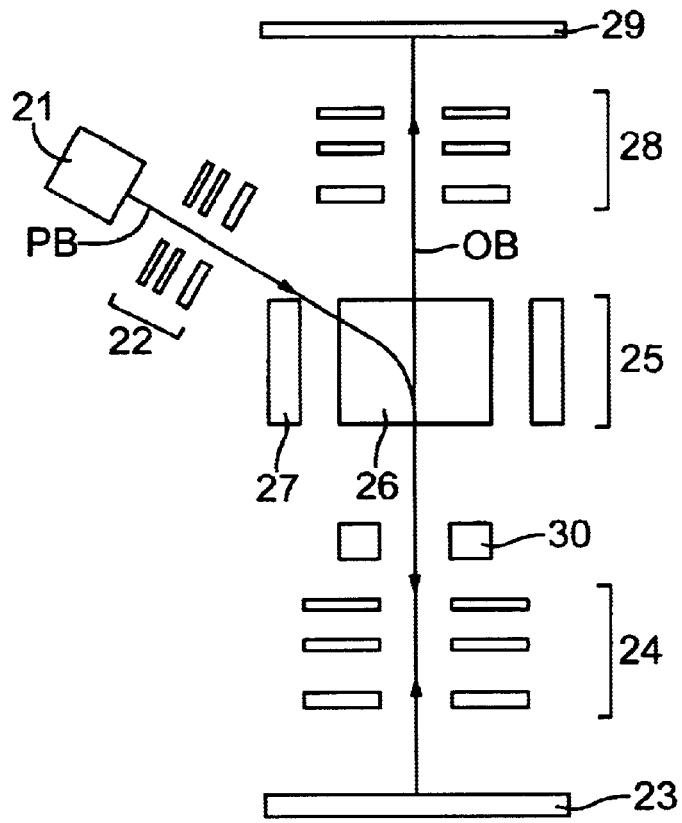
FIG. 1 is an elevational schematic drawing showing certain features of a conventional charged-particle-beam (CPB) mapping projection-optical system.
Figure 13:
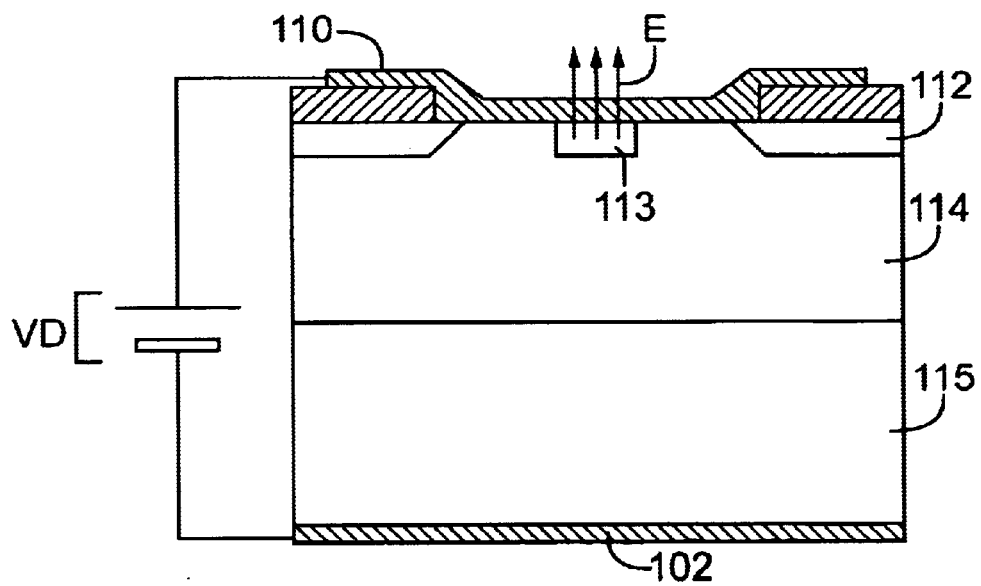
FIG. 13 is a schematic elevational view of a GaAs Schottky junction emitter as described in Representative Embodiment 5.
Figure 14:
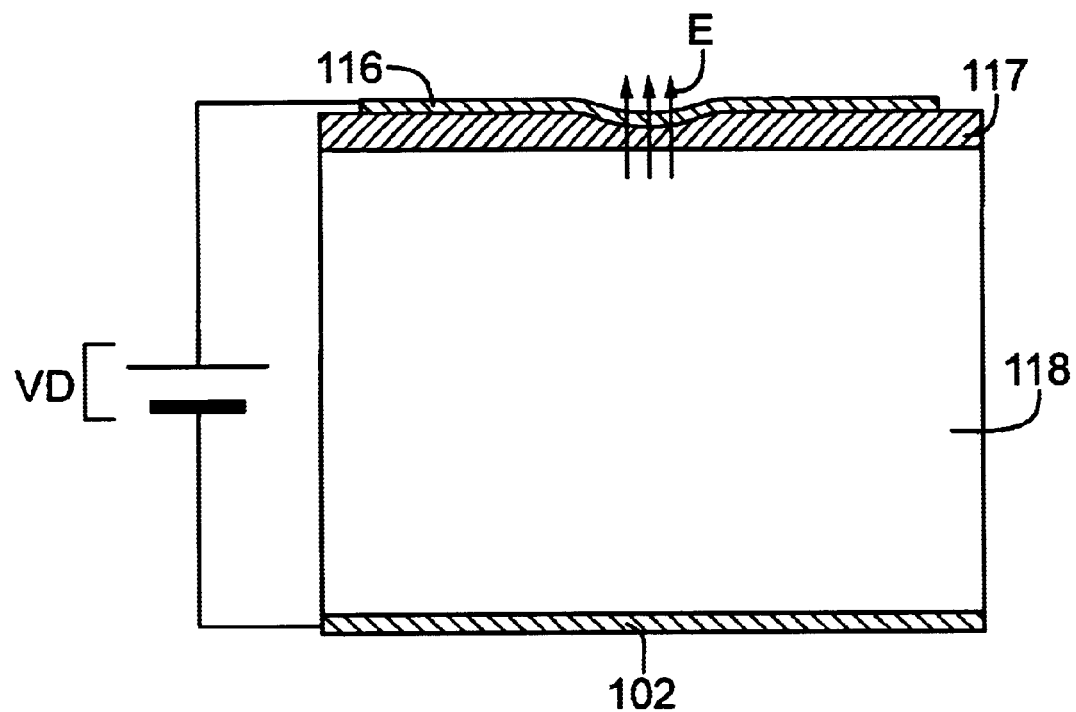
FIG. 14 is a schematic elevational view of a MOS-type emitter as described in Representative Embodiment 5.

Reference is now made to FIGS. 13 and 14 which depict alternative hot-electron emitters.

FIG. 13 schematically depicts a GaAs Schottky junction emitter. A p$^+$-GaAs layer 115 is formed on one surface of a p-GaAs substrate 114, and a rear metal electrode 102 (desirably aluminum) having a thickness of, e.g., 10 nm is formed on the other surface of the p-GaAs substrate 114. A p$^+$-GaAs field 113 (having a diameter of, e.g., several micrometers) and an n$^+$-GaAs field 112 are formed on specific regions of the p-GaAs substrate 114 to form Schottky junctions. Whenever a reverse bias is impressed on the rear electrode 102 and on an emitter electrode 110, cascade multiplication is induced. Some of the resulting current that flows through the junction is emitted into a vacuum as the evaluation electron beam E.

Turning now to FIG. 14, a MOS-type emitter is schematically shown. In this embodiment, an insulating film 117 (desirably SiO$_2$, approximately 10-nm thick) is formed by thermal oxidation on the surface of an n-Si substrate 18. Atop the insulating film 117 is formed a gate electrode 116 (desirably made of aluminum or amorphous silicon, and having about the same thickness as the insulating film 117). A rear metal electrode 102 (desirably aluminum) is formed on the rear surface of the substrate 118. Whenever a normal bias is impressed on the rear electrode 102 and the gate electrode 116, an electron beam E is emitted.

In the hot-electron emitters of FIGS. 13 and 14, the peak value of kinetic energy in the kinetic-energy distribution of the evaluation beam E is zero to several eV and the surface potential is held at a constant value. Such a kinetic energy of the evaluation beam is essentially equal to the kinetic energy of a secondary beam emitted from the specimen in the CPB mapping microscope. It is possible to bring the kinetic energy of the evaluation beam E even closer to the kinetic energy of the secondary beam by adjusting the structural constants, bias, and gate voltage of the emitter. Furthermore, since the surface potential of the emitter is constant, the emitter imparts no effect on the imaging performance of the secondary optical system.

Thus, with such emitters, the optical performance of the secondary optical system of a CPB mapping microscope can be evaluated without having to utilize the primary optical system. Furthermore, by making the kinetic energy of the electron beam emitted from the emitter variable, it is possible to separately quantitatively evaluate, e.g., chromatic aberration exhibited by the secondary optical system.

Whereas the invention has been described in connection with multiple representative embodiments, it will be understood that the invention is not limited to those embodiments. On the contrary, the invention is intended to encompass all alternatives, modifications, and equivalents as may be included within the spirit and scope of the invention as defined by the appended claims.

What is claimed is:

1. A charged-particle-beam mapping projection-optical system, comprising:
   (a) an irradiation optical system that directs an irradiation charged particle beam along a first axis from an irradiation-beam source;
   (b) an ExB beam separator configured and situated to receive the irradiation beam from the irradiation optical system and to direct the irradiation beam downstream of the ExB beam separator;
   (c) an objective optical system configured and situated to receive the irradiation beam from the ExB beam separator, direct the irradiation beam to be incident on a surface of a specimen located at a position downstream of the objective optical system, receive an observation charged particle beam generated by impingement of the irradiation beam on the specimen surface, and direct the observation beam to the ExB beam separator, wherein the ExB beam separator causes the observation beam to propagate along a second axis having a direction different than the first axis;
   (d) an imaging optical system configured and situated to receive the observation beam from the ExB beam separator and to direct the observation beam from the ExB beam separator to a detector; and
   (e) an adjustment-beam source configured to emit an adjustment charged particle beam, the adjustment-beam source being situatable at the specimen position so as to direct the adjustment beam, in place of the observation beam, through the objective and imaging optical systems to the detector.

2. The system of claim 1, wherein the adjustment-beam source produces the adjustment beam having an emission profile, at the specimen position, corresponding to at least one of a dot, a line, a plane, a cross, or an L-shaped profile.

3. The system of claim 1, wherein the adjustment beam is an electron beam.

4. The system of claim 1, wherein the adjustment-beam source produces the adjustment beam having a kinetic energy equal to a kinetic energy of the observation beam as generated at the specimen surface.

5. The system of claim 1, wherein the adjustment-beam source comprises a cold cathode.

6. The system of claim 1, further comprising an electrode situated object-wise of the objective optical system, the electrode being operable to generate a potential relative to the adjustment-beam source sufficient to accelerate the adjustment beam as the adjustment beam propagates to the detector.

7. In a method for operating a charged-particle-beam mapping projection microscope, wherein an irradiation charged particle beam is directed along a first axis from an irradiation-beam source through an irradiation optical system to an ExB beam separator, then passed through the ExB beam separator and through an objective optical system so as to cause the irradiation beam to impinge on a surface of a specimen at an object surface and generate, from the impingement, an observation charged particle beam propagating from the specimen toward the objective optical system; and the observation beam is passed through the objective optical system and the ExB beam separator along a second axis having a different direction than the first axis, and then through an imaging optical system to a detector, a process for adjusting the objective optical system and imaging optical system, comprising:
(a) at the object surface, replacing the specimen with an adjustment-beam source that emits an adjustment charged particle beam; and
(b) while passing the adjustment beam through the objective optical system, the ExB beam separator, and the imaging optical system, applying electrical power only to the objective optical system and determining one or more of an axial alignment and an aberration characteristic of the objective optical system.

8. The method of claim 7, further comprising the step of adjusting the one or more of an axial alignment and an aberration characteristic of the objective optical system.

9. The method of claim 7, further comprising the step, after step (b), of applying electrical power to the imaging optical system as well as the objective optical system, and determining one or more of an axial alignment and an aberration characteristic of the imaging optical system.

10. The method of claim 9, further comprising the step of adjusting the one or more of an axial alignment and an aberration characteristic of the imaging optical system.

11. A charged-particle-beam mapping projection-optical system, comprising:
(a) an irradiation optical system that directs an irradiation charged particle beam along a first axis from an irradiation-beam source;
(b) an ExB beam separator configured and situated to receive the irradiation beam from the irradiation optical system and to direct the irradiation beam downstream of the ExB beam separator;
(c) an objective optical system configured and situated to receive the irradiation beam from the ExB beam separator, direct the irradiation beam to be incident on a specimen surface located at an object-surface plane downstream of the objective optical system, receive an observation charged particle beam generated by impingement of the irradiation beam on the specimen surface, and direct the observation beam to the ExB beam separator, wherein the ExB beam separator causes the observation beam to propagate along a second axis having a direction different than the first axis;
(d) an imaging optical system configured and situated to receive the observation beam from the ExB beam separator and to direct the observation beam from the ExB beam separator to a first detector;
(e) an alignment-beam source configured to emit an alignment beam with respect to the object-surface so as to cause the alignment beam to acquire data regarding an alignment characteristic of the object surface; and
(f) an alignment optical system situated off-axis from the objective and imaging optical systems and configured to direct the alignment beam from the object surface to a second detector that detects the data.

12. The system of claim 11, wherein the alignment-beam source is suitable at and movable within the object-surface plane.

13. The system of claim 12, wherein the alignment-beam source is defined on a fiducial plate.

14. The system of claim 13, wherein the fiducial plate comprises a fiducial mark.

15. The system of claim 11, wherein the alignment beam is a beam of light.

16. The system of claim 11, wherein the alignment beam is a charged particle beam.

17. The system of claim 16, wherein the alignment beam is an electron beam and the off-axis optical system is a scanning electron microscope.

18. The system of claim 16, wherein the alignment-beam source has an emission profile at the object surface, the emission profile being at least one of a dot, a line, a cross, or an L-shaped profile.

19. The system of claim 16, wherein the alignment beam has a kinetic energy equal to a kinetic energy of the observation beam.

20. The system of claim 16, wherein the alignment-beam source comprises a cold cathode.

21. The system of claim 16, wherein an electrical potential exists between alignment-beam source and an object-wise surface of the objective optical system, the potential causing an acceleration of the alignment beam as the alignment beam propagates through the objective optical system.

22. In a method for operating a charged-particle-beam mapping projection microscope, wherein an irradiation charged particle beam is directed along a first axis from an irradiation-beam source through an irradiation optical system to an ExB beam separator, then passed through the ExB beam separator and through an objective optical system so as to cause the irradiation beam to impinge on a surface of a specimen at an object surface and generate, from the impingement, an observation charged particle beam propagating from the specimen toward the objective optical system; and the observation beam is passed through the objective optical system and the ExB beam separator along a second axis having a different direction than the first axis, and then through an imaging optical system to a detector, a process for adjusting the objective optical system and imaging optical system, comprising:
(a) placing an adjustment-beam source at the object surface, the adjustment-beam source being operable to emit an adjustment charged particle beam; and
(b) adjusting an electrical potential and an electrical current applied to the ExB beam separator so as to align an image formed on the detector by the adjustment-beam source when electrical potential and electrical current are not applied to the ExB beam separator with an image formed on the detector by the adjustment-beam source when electrical potential and electrical current are applied to the ExB beam separator.

23. The method of claim 22, wherein:

the imaging optical system comprises a stigmator that corrects aberration in the image formed on the detector; and step (b) comprises adjusting an electrical energy applied to at least one of the objective optical system and the imaging optical system while adjusting the electrical potential applied to the detector.

24. The method of claim 22, wherein the adjustment beam is an electron beam.

25. The method of claim 24, wherein the adjustment beam has a kinetic energy equal to a kinetic energy of the observation beam.

26. The method of claim 22, further comprising providing a potential difference between the adjustment-beam source and a specimen-wise surface of the objective optical system, the potential difference serving to accelerate the adjustment beam.

27. A charged-particle-beam mapping projection-optical system, comprising:

(a) an irradiation optical system that directs an irradiation charged particle beam along a first axis from an irradiation-beam source;

(b) an ExB beam separator configured and situated to receive the irradiation beam from the irradiation optical system and to direct the irradiation beam downstream of the ExB beam separator;

(c) an objective optical system configured and situated to receive the irradiation beam from the ExB beam separator, direct the irradiation beam to be incident on a specimen surface located at an object-surface plane downstream of the objective optical system, receive an observation charged particle beam generated by impingement of the irradiation beam on the specimen surface, and direct the observation beam to the ExB beam separator, wherein the ExB beam separator causes the observation beam to propagate along a second axis having a direction different than the first axis;

(d) an imaging optical system configured and situated to receive the observation beam from the ExB beam separator and to direct the observation beam from the ExB beam separator to a first detector;

(e) an adjustment-beam source configured to emit an adjustment beam with respect to the object-surface so as to cause the adjustment beam to acquire data regarding a position of the object surface; and (f) the ExB beam separator being connected to a variable-power supply to permit an electrical potential and an electrical current applied to the ExB beam separator to be adjusted as required such that an image formed on the detector by the adjustment beam when electrical potential and electrical current are not applied to the ExB beam separator is aligned with an image formed on the detector by the adjustment beam when electrical potential and electrical current are applied to the ExB beam separator.

28. A charged-particle-beam mapping projection-optical system, comprising:

(a) an irradiation optical system that directs an irradiation charged particle beam along a first axis from an irradiation-beam source;

(b) an ExB beam separator configured and situated to receive the irradiation beam from the irradiation optical system and to direct the irradiation beam downstream of the ExB beam separator;

(c) an objective optical system configured and situated to receive the irradiation beam from the ExB beam separator, direct the irradiation beam to be incident on a specimen surface located at an object-surface plane downstream of the objective optical system, receive an observation charged particle beam generated by impingement of the irradiation beam on the specimen surface, and direct the observation beam to the ExB beam separator, wherein the ExB beam separator causes the observation beam to propagate along a second axis having a direction different than the first axis;

(d) an imaging optical system configured and situated to receive the observation beam from the ExB beam separator and to direct the observation beam from the ExB beam separator to a first detector;

(e) an adjustment-beam source configured to emit an adjustment beam with respect to the object-surface so as to cause the adjustment beam to acquire data regarding a position of the object surface; and (f) an evaluation chart configured so as to be insertable at the object-surface plane, the evaluation chart spontaneously emitting an evaluation electron beam for evaluating an optical-performance characteristic of the imaging optical system.

29. The system of claim 28, wherein the evaluation electron beam has a kinetic energy that is equal to a kinetic energy of the observation beam.

30. The system of claim 28, wherein the evaluation electron beam has an emission profile selected from the group consisting of a dot-shaped profile, a line-shaped profile, or a planar profile.

31. The system of claim 28, wherein the evaluation chart comprises a hot-electron emitter.

* * * * *

UNITED STATES PATENT AND TRADEMARK OFFICE
CERTIFICATE OF CORRECTION

PATENT NO. : 6,765,217 B1
DATED : July 20, 2004
INVENTOR(S) : Nishimura et al.

It is certified that error appears in the above-identified patent and that said Letters Patent is hereby corrected as shown below:

Column 1,
Lines 20-21, "electron microscopes"." should be -- electron microscopes." --.
Line 51, "returns" should be -- return --.

Column 2,
Line 9, "to accurately observe" should be -- to observe --.
Line 10, "specimen 23" should be -- specimen 23 accurately. --.
Line 11, "able to independently adjust" should be -- able independently to adjust --.
Line 43, "microscope an" should be -- microscope, an --.
Lines 59 and 62, "electomagnetic pole" should be -- electromagnetic-pole --.
Line 65, "to continually readjust" should be -- to readjust --.
Line 66, "system." should be -- system continually. --.

Column 4,
Line 64, "object-surface" should be -- object-surface plane --.
Line 66, "object surface." should be -- object-surface plane. --.

Column 5
Lines 1-2, "object surface" should be -- object-surface plane --.

Column 6,
Line 31, "object-surface" should be -- object-surface plane --.

Column 7,
Line 6, "object-surface" should be -- object-surface --.

Column 8,
Lines 61-62, "illumination The" should be -- illumination. The --.

Column 9,
Line 13, "stop F2." should be -- stop FS2. --.
Lines 58-59, "The reason the trajectory is bent is because," should be -- The trajectory is bent because, --.

Column 13,
Line 47, "filter 71" should be -- fiber 71 --.

Column 18,
Line 64, "primary bean" should be -- primary beam --.

UNITED STATES PATENT AND TRADEMARK OFFICE
CERTIFICATE OF CORRECTION

PATENT NO. : 6,765,217 B1
DATED : July 20, 2004
INVENTOR(S) : Nishimura et al.

It is certified that error appears in the above-identified patent and that said Letters Patent is hereby corrected as shown below:

Column 20,
Line 33, "FIG. 11" should be -- FIG. -11 --.

Column 21,
Line 48, "14 which" should be -- 14, which --.

Column 22,
Line 23, "Furthermore, by" should be -- Furthermore, for example, by --.
Lines 24-25, "possible to separately quantitatively evaluate, e.g., chromatic" should be -- possible separately to evaluate, in a quantitative manner, chromatic --.

Column 23,
Lines 42, 45 and 50, "The method of" should be -- The process of --.

Column 24,
Lines 13, 15 and 18, "object-surface" should be -- object-surface plane --.
Line 20, "suitable" should be -- situatable --.
Line 34, "object surface" should be -- object-surface plane --.

Column 25,
Lines 7, 15, 17 and 20, "The method of" should be -- The process of --.
Lines 52 and 54, "object-surface" should be -- object-surface plane --.

Column 26,
Line 38, "object-surface" should be -- object-surface plane --.
Line 40, "object surface" should be -- object-surface plane --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,765,217 B1 Page 1 of 1
APPLICATION NO. : 09/302075
DATED : July 20, 2004
INVENTOR(S) : Nishimura et al.

It is certified that error appears in the above-identified patent and that said Letters Patent is hereby corrected as shown below:

Title page,

Insert below (22) Filed:

--(30) Foreign Application Priority Data

| April 28, 1998 | (JP) | 10-134473 |
| June 12, 1998 | (JP) | 10-181499 |
| December 22, 1998 | (JP) | 10-364416-- |

Signed and Sealed this

Sixth Day of February, 2007

JON W. DUDAS
*Director of the United States Patent and Trademark Office*